(12) United States Patent
Simon et al.

(10) Patent No.: US 8,660,635 B2
(45) Date of Patent: Feb. 25, 2014

(54) METHOD AND APPARATUS FOR OPTIMIZING A COMPUTER ASSISTED SURGICAL PROCEDURE

(75) Inventors: David Simon, Boulder, CO (US); Mark S. Lent, Brooklyn Park, MN (US); Ruchika Singhal, Minneapolis, MN (US); Andrew N. Csavoy, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1225 days.

(21) Appl. No.: 11/683,796

(22) Filed: Mar. 8, 2007

(65) Prior Publication Data

US 2008/0081982 A1 Apr. 3, 2008

Related U.S. Application Data

(60) Provisional application No. 60/848,442, filed on Sep. 29, 2006.

(51) Int. Cl.
*A61B 5/05* (2006.01)
(52) U.S. Cl.
USPC ............ 600/424; 600/423; 600/427; 600/407
(58) Field of Classification Search
USPC ........... 600/407–436; 324/306–309, 318–322
See application file for complete search history.

(56) References Cited

U.S. PATENT DOCUMENTS

| | | | |
|---|---|---|---|
| 1,576,781 A | 3/1926 | Phillips | |
| 1,735,726 A | 11/1929 | Bornhardt | |
| 2,407,845 A | 9/1946 | Nemeyer | |
| 2,650,588 A | 9/1953 | Drew | |
| 2,697,433 A | 12/1954 | Sehnder | |
| 3,016,899 A | 1/1962 | Stenvall | |
| 3,017,887 A | 1/1962 | Heyer | |
| 3,061,936 A | 11/1962 | Dobbeleer | |
| 3,073,310 A | 1/1963 | Mocarski | |
| 3,109,588 A | 11/1963 | Polhemus et al. | |
| 3,294,083 A | 12/1966 | Alderson | |
| 3,367,326 A | 2/1968 | Frazier | |
| 3,439,256 A | 4/1969 | Kahne | |
| 3,577,160 A | 5/1971 | White | |
| 3,614,950 A | 10/1971 | Rabey | |

(Continued)

FOREIGN PATENT DOCUMENTS

| | | |
|---|---|---|
| CA | 964149 A1 | 3/1975 |
| DE | 3042343 A1 | 6/1982 |

(Continued)

OTHER PUBLICATIONS

International Search Report and Written Opinion for PCT/US2007/009931 mailed Nov. 14, 2007, claiming priority to U.S. Appl. No. 11/683,796, filed Mar. 8, 2007.

(Continued)

*Primary Examiner* — Tse Chen
*Assistant Examiner* — Joel F Brutus
(74) *Attorney, Agent, or Firm* — Harness, Dickey & Pierce, PLC

(57) ABSTRACT

A method and apparatus for optimizing a computer assisted procedure is provided. A method and apparatus for performing a procedure is also provided. Data can be accessed and processed to optimize and perform a procedure. The data can be augmented or supplemented with patient specific data.

52 Claims, 10 Drawing Sheets

(56) References Cited

U.S. PATENT DOCUMENTS

| | | |
|---|---|---|
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |

(56) References Cited

U.S. PATENT DOCUMENTS

| | | |
|---|---|---|
| 5,107,843 A | 4/1992 | Aarnio et al. |
| 5,107,862 A | 4/1992 | Fabian et al. |
| 5,109,194 A | 4/1992 | Cantaloube |
| 5,117,836 A | 6/1992 | Millar |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,484,437 A | 1/1996 | Michelson |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,531,673 A | 7/1996 | Helenowski |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,558,638 A | 9/1996 | Evers et al. |
| 5,566,681 A | 10/1996 | Manwaring et al. |
| 5,568,384 A | 10/1996 | Robb et al. |
| 5,568,809 A | 10/1996 | Ben-haim |

(56) References Cited

U.S. PATENT DOCUMENTS

| | | |
|---|---|---|
| 5,571,109 A | 11/1996 | Bertagnoli et al. |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,690,117 A | 11/1997 | Gilbert |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,733,259 A | 3/1998 | Valcke et al. |
| 5,735,278 A | 4/1998 | Hoult et al. |
| 5,735,814 A | 4/1998 | Elsberry et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,772,661 A | 6/1998 | Michelson |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,824,048 A | 10/1998 | Tuch |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,970,499 A | 10/1999 | Smith et al. |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf et al. |
| 5,987,349 A | 11/1999 | Schulz |
| 5,987,960 A | 11/1999 | Messner et al. |
| 5,999,837 A | 12/1999 | Messner et al. |

(56) References Cited

U.S. PATENT DOCUMENTS

| | | | |
|---|---|---|---|
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,026,316 A | 2/2000 | Kucharczyk et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,064,904 A | 5/2000 | Yanof et al. |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,194,639 B1 | 2/2001 | Botella et al. |
| 6,198,794 B1 | 3/2001 | Peshkin et al. |
| 6,201,387 B1 | 3/2001 | Govari |
| 6,201,988 B1 | 3/2001 | Bourland et al. |
| 6,203,497 B1 | 3/2001 | Dekel et al. |
| 6,206,885 B1 | 3/2001 | Ghahremani et al. |
| 6,211,666 B1 | 4/2001 | Acker |
| 6,223,067 B1 | 4/2001 | Vilsmeier et al. |
| 6,233,476 B1 | 5/2001 | Strommer et al. |
| 6,246,231 B1 | 6/2001 | Ashe |
| 6,259,942 B1 | 7/2001 | Westermann et al. |
| 6,273,896 B1 | 8/2001 | Franck et al. |
| 6,283,951 B1 | 9/2001 | Flaherty et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,332,089 B1 | 12/2001 | Acker et al. |
| 6,341,231 B1 | 1/2002 | Ferre et al. |
| 6,348,058 B1 | 2/2002 | Melkent et al. |
| 6,351,659 B1 | 2/2002 | Vilsmeier |
| 6,381,485 B1 | 4/2002 | Hunter et al. |
| 6,385,483 B1 | 5/2002 | Uber, III et al. |
| 6,390,097 B1 | 5/2002 | Chandra |
| 6,402,689 B1 | 6/2002 | Scarantino et al. |
| 6,406,426 B1 | 6/2002 | Reuss et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,464,662 B1 | 10/2002 | Raghavan et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,482,182 B1 | 11/2002 | Carroll et al. |
| 6,484,049 B1 | 11/2002 | Seeley et al. |
| 6,490,475 B1 | 12/2002 | Seeley et al. |
| 6,491,699 B1 | 12/2002 | Henderson et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,516,212 B1 | 2/2003 | Bladen et al. |
| 6,526,415 B2 | 2/2003 | Smith et al. |
| 6,527,443 B1 | 3/2003 | Vilsmeier et al. |
| 6,531,152 B1 | 3/2003 | Lerner et al. |
| 6,549,803 B1 | 4/2003 | Raghavan et al. |
| 6,551,325 B2 | 4/2003 | Neubauer et al. |
| 6,567,690 B2 | 5/2003 | Giller et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,658,396 B1 | 12/2003 | Tang et al. |
| 6,671,538 B1 | 12/2003 | Ehnholm et al. |
| 6,694,162 B2 | 2/2004 | Hartlep et al. |
| 6,701,179 B1 | 3/2004 | Martinelli et al. |
| 6,740,883 B1 | 5/2004 | Stodilka et al. |
| 6,755,789 B2 | 6/2004 | Stringer et al. |
| 6,828,966 B1 | 12/2004 | Gavriliu et al. |
| 6,901,287 B2 | 5/2005 | Davis et al. |
| 6,905,492 B2 | 6/2005 | Zvuloni et al. |
| 6,973,718 B2 | 12/2005 | Sheppard, Jr. et al. |
| 6,979,348 B2 | 12/2005 | Sundar |
| 6,982,282 B2 | 1/2006 | Lambert et al. |
| 7,011,814 B2 | 3/2006 | Suddarth et al. |
| 7,047,235 B2 | 5/2006 | Yang et al. |
| 7,072,705 B2 | 7/2006 | Miga et al. |
| 7,081,088 B2 | 7/2006 | Geiger |
| 7,092,748 B2 | 8/2006 | Valdes Sosa et al. |
| 7,103,399 B2 | 9/2006 | Miga et al. |
| 7,167,180 B1 | 1/2007 | Shibolet |
| 7,194,295 B2 | 3/2007 | Vilsmeier |
| 7,313,430 B2 | 12/2007 | Urquhart et al. |
| 7,599,730 B2 | 10/2009 | Hunter et al. |
| 2001/0007918 A1 | 7/2001 | Vilsmeier et al. |
| 2002/0069215 A1* | 6/2002 | Orbanes et al. ............... 707/500 |
| 2002/0095081 A1 | 7/2002 | Vilsmeier et al. |
| 2003/0028118 A1 | 2/2003 | Dupree et al. |
| 2003/0078485 A1 | 4/2003 | Hartlep |
| 2003/0101081 A1 | 5/2003 | Putnam et al. |
| 2003/0114752 A1 | 6/2003 | Henderson et al. |
| 2003/0191408 A1 | 10/2003 | Montgomery |
| 2004/0024309 A1 | 2/2004 | Ferre et al. |
| 2004/0039259 A1 | 2/2004 | Krause et al. |
| 2004/0068172 A1 | 4/2004 | Nowinski et al. |
| 2004/0092809 A1 | 5/2004 | DeCharms |
| 2004/0097806 A1 | 5/2004 | Hunter et al. |
| 2004/0107210 A1 | 6/2004 | Yang et al. |
| 2004/0138551 A1 | 7/2004 | Hartlep et al. |
| 2004/0158313 A1 | 8/2004 | Altman |
| 2004/0210124 A1 | 10/2004 | Nowinski et al. |
| 2004/0215071 A1 | 10/2004 | Frank et al. |
| 2004/0215162 A1 | 10/2004 | Putz |
| 2004/0236554 A1 | 11/2004 | Raghavan et al. |
| 2004/0240753 A1 | 12/2004 | Hu et al. |
| 2004/0254437 A1 | 12/2004 | Hauck et al. |
| 2005/0002918 A1 | 1/2005 | Strauss et al. |
| 2005/0004617 A1* | 1/2005 | Dawant et al. ................ 607/45 |
| 2005/0004909 A1* | 1/2005 | Stevenson et al. ................ 707/5 |
| 2005/0018885 A1 | 1/2005 | Chen et al. |
| 2005/0031210 A1 | 2/2005 | Shen et al. |
| 2005/0049486 A1 | 3/2005 | Urquhart et al. |
| 2005/0070781 A1 | 3/2005 | Dawant et al. |
| 2005/0084146 A1 | 4/2005 | Watson et al. |
| 2005/0085714 A1 | 4/2005 | Foley et al. |
| 2005/0085720 A1 | 4/2005 | Jascob et al. |
| 2005/0101855 A1 | 5/2005 | Miga et al. |
| 2005/0111621 A1 | 5/2005 | Riker et al. |
| 2005/0148859 A1 | 7/2005 | Miga et al. |
| 2005/0171558 A1 | 8/2005 | Abovitz et al. |
| 2005/0245814 A1 | 11/2005 | Anderson et al. |
| 2006/0017749 A1* | 1/2006 | McIntyre et al. ............. 345/664 |
| 2006/0084867 A1 | 4/2006 | Tremblay et al. |
| 2006/0182321 A1 | 8/2006 | Hu et al. |
| 2006/0217733 A1 | 9/2006 | Plassky et al. |
| 2007/0021668 A1 | 1/2007 | Boese et al. |

(56) References Cited

U.S. PATENT DOCUMENTS

| | | |
|---|---|---|
| 2007/0100226 A1 | 5/2007 | Yankelevitz et al. |
| 2008/0081982 A1 | 4/2008 | Simon et al. |

FOREIGN PATENT DOCUMENTS

| | | |
|---|---|---|
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 | 11/2002 |
| EP | 0062941 | 10/1982 |
| EP | 0119660 A1 | 9/1984 |
| EP | 0155857 | 9/1985 |
| EP | 0319844 | 6/1989 |
| EP | 0326768 A2 | 8/1989 |
| EP | 0350996 A1 | 1/1990 |
| EP | 0419729 A1 | 4/1991 |
| EP | 0427358 | 5/1991 |
| EP | 0456103 | 11/1991 |
| EP | 0469966 A1 | 2/1992 |
| EP | 0581704 A1 | 2/1994 |
| EP | 0651968 A1 | 5/1995 |
| EP | 0655138 A1 | 5/1995 |
| EP | 0894473 A2 | 2/1999 |
| EP | 0908146 A2 | 4/1999 |
| EP | 0930046 A2 | 7/1999 |
| EP | 1344187 | 9/2003 |
| EP | 1396233 | 3/2004 |
| EP | 1406203 | 4/2004 |
| EP | 1442715 A2 | 8/2004 |
| EP | 1474782 | 11/2004 |
| EP | 1597701 | 11/2005 |
| EP | 1603076 | 12/2005 |
| EP | 1691687 | 8/2006 |
| EP | 1692633 | 8/2006 |
| EP | 1692657 | 8/2006 |
| EP | 1713015 | 10/2006 |
| FR | 2417970 A1 | 9/1979 |
| FR | 2618211 | 1/1989 |
| GB | 2094590 A | 9/1982 |
| GB | 2164856 A | 4/1986 |
| JP | 62327 | 6/1983 |
| JP | 61-94639 A | 10/1984 |
| JP | 63240851 A | 10/1988 |
| JP | 2765738 T | 4/1991 |
| JP | 3267054 | 11/1991 |
| WO | WO-8809151 A1 | 12/1988 |
| WO | WO-8905123 | 6/1989 |
| WO | WO-9005494 A1 | 5/1990 |
| WO | WO-9103982 A1 | 4/1991 |
| WO | WO-9104711 A1 | 4/1991 |
| WO | WO-9107726 A1 | 5/1991 |
| WO | WO-9203090 A1 | 3/1992 |
| WO | WO-9206645 A1 | 4/1992 |
| WO | WO-9404938 A1 | 3/1994 |
| WO | WO-9423647 A1 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |
| WO | WO-9838908 A1 | 9/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |
| WO | WO-9952094 A1 | 10/1999 |
| WO | WO-9960939 A1 | 12/1999 |
| WO | WO-0007652 | 2/2000 |
| WO | WO-0010034 | 2/2000 |
| WO | WO-0130437 A1 | 5/2001 |
| WO | WO-0243003 | 5/2002 |
| WO | WO-02093292 | 11/2002 |
| WO | WO-02097735 | 12/2002 |
| WO | WO-02098292 | 12/2002 |
| WO | WO-03039600 A1 | 5/2003 |
| WO | WO-03060827 | 7/2003 |
| WO | WO-2004077359 | 9/2004 |
| WO | WO-2004096018 | 11/2004 |
| WO | WO-2005002444 | 1/2005 |
| WO | WO-2005048844 | 6/2005 |
| WO | WO-2005052838 | 6/2005 |
| WO | WO-2005057493 | 6/2005 |
| WO | WO-2005057498 | 6/2005 |
| WO | WO-2005084542 | 9/2005 |
| WO | WO-2005096227 | 10/2005 |
| WO | WO-2005111931 | 11/2005 |
| WO | WO-2006011850 | 2/2006 |
| WO | WO-2006017053 | 2/2006 |
| WO | WO-2006017392 | 2/2006 |
| WO | WO-2006028416 | 3/2006 |
| WO | WO-2006028474 | 3/2006 |
| WO | WO-2006069250 | 6/2006 |
| WO | WO-2006083236 | 8/2006 |
| WO | WO-2006088429 | 8/2006 |

OTHER PUBLICATIONS

International Preliminary Report on Patentability for PCT/US2007/009931 mailed Jan. 20, 2009, claiming priority to U.S. Appl. No. 11/683,796, filed Mar. 8, 2007.

iPlan® Stereotaxy Software, BrainLab, http://www.brainlab.com/scripts/website_english.asp?menuDeactivate=1&articleID=1842&articleTypeID=27&pageTypeID=4&article_short_headline=iPlan%AE%20Stereotaxy printed Apr. 1, 2009.

NeuroSight™ Cranial Module, Radionics™, Jul. 27, 2003 http://www.radionics.com/products/frameless/omnisight/omnisight_modules.shtml#neuro accessed and printed on Apr. 1, 2009 through the Wayback Machine at http://www.archive.org/web/web.php.

VectorVision® cranial Navigation Software, BrainLab, http://www.brainlab.com/scripts/website_english.asp?menuDeactivate=1&articleID=593&articleTypeID=27&pageTypeID=4&article_short_headline=VectorVision%AE%20%20cranial printed Apr. 1, 2009.

Versweyveld, Leslie, "Scientists in Singapore develop Virtual Brain Bench for stereotactic frame neurosurgery," VMW Virtual Medical Worlds Monthly, printed Apr. 1, 2009 (3 pages).

G. Champleboux, et al., "Accurate Calibration of Cameras and Range Imaging Sensors: the NPBS Method," Proceedings of the IEEE International Conference on Robotics and Automation, Nice, France, May 1992.

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 4, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensional Computer Reconstructions of Brain Lesions from Surface Contours Provided by Computed Tomography: A Prospectus," Neurosurgery, vol. 11, No. 1, Part 1, 1982, pp. 73-84.

(56) References Cited

OTHER PUBLICATIONS

Benzel et al., "Magnetic Source Imaging: a Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Cinquin et al., "Computer Assisted Medical Interventions," IEEE Engineering in Medicine and Biology, May/Jun. 1995, pp. 254-263.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. 1996, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG (1997).

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

International Preliminary Report on Patentability for PCT/US2007/009820 mailed Oct. 30, 2008 claiming benefit of U.S. Appl. No. 11/409,499.

International Search Report and Written Opinion for PCT/US2007/009820 mailed Sep. 21, 2007 claiming benefit of U.S. Appl. No. 11/409,499.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

(56) References Cited

OTHER PUBLICATIONS

Kato, A., et al., A frameless, armless navigational system for computer-assisted neurosurgery, J. Neurosurg., vol. 74, pp. 845-849 (May 1991).
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Image guided operating robot: a clinical application in stereotactic neurosurgery," Proceedings of the 1992 IEEE Internation Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Leksell et al., "Stereotaxis and Tomography—A Technical Note," Acta Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Merloz, et al., "Computer Assisted Spine Surgery", Clinical Assisted Spine Surgery, No. 337 (1997) pp. 86-96.
Ng, W.S. et al., Robotic Surgery—A First-Hand Experience in Transurethral Resection of the Prostate Surgery, IEEE Eng. in Med. and Biology, pp. 120-125 (Mar. 1993).
Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Penn, R.D., et al., Stereotactic Surgery with Image Processing of Computerized Tomographic Scans, Neurosurgery, vol. 3, No. 2, pp. 157-163 (Sep.-Oct. 1978).
Phillips et al., "Image Guided Orthopaedic Surgery Design and Analysis," Trans Inst. MC, vol. 17, No. 5, 1995, pp. 251-264.
Reinhardt et al., "CT-Guided 'Real Time' Stereotaxy," Acta Neurochirurgica, 1989.
Reinhardt, H., et al., A Computer-Assisted Device for Intraoperative CT-Correlated Localization of Brain Tumors, pp. 51-58 (1988).
Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).
Roberts et al., "A frameless stereotaxic integration of computerized tomographic imaging and the operating microscope," J. Neurosurg., vol. 65, Oct. 1986, pp. 545-549.
Rosenbaum et al., "Computerized Tomography Guided Stereotaxis: A New Approach," Applied Neurophysiology, vol. 43, No. 3-5, 1980, pp. 172-173.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Smith et al., "Computer Methods for Improved Diagnostic Image Display Applied to Stereotactic Neurosurgery," Automedical, vol. 14, 1992, pp. 371-382 (4 unnumbered pages).
Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.
Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

(56) References Cited

OTHER PUBLICATIONS

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images" (1997) pp. 119-128.

Schueler, Beth, et al., "Correction of Image Intensifier Distortion for Three-Dimensional X-ray Angiography," Proceedings, SPIE—the International Society for Optical Engineering, Medical Imaging 1995—Physics of Medical Imaging, pp. 273-279 (San Diego, California, Feb. 26-27, 1995).

International Search Report and Written Opinion mailed Apr. 11, 2009 for PCT/US2009/051341 filed Jul. 22, 2009.

Bryan, "Bryan Cervical Disc System Single Level Surgical Technique", Spinal Dynamics, 2002, pp. 1-33.

Bucholz, R.D., et al., Intraoperative Ultrasonic Brain Shift Monitor and Analysis, Stealth Station Marketing Brochure (2 pages) (undated).

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," International Advanced Robotics Programme, Sep. 1989, pp. 63-65.

Friets, E.M., et al. A Frameless Stereotaxic Operating Microscope for Neurosurgery, IEEE Trans. on Biomed. Eng., vol. 36, No. 6, pp. 608-617 (Jun. 1989).

Galloway, R.L., Jr. et al, Optical localization for interactive, image-guided neurosurgery, SPIE, vol. 2164, (May 1, 1994) pp. 137-145.

Guthrie, B.L., Graphic-Interactive Cranial Surgery: The Operating Arm System, Handbook of Stereotaxy Using the CRW Apparatus, Chapter 13 (1994) pp. 193-211.

Klimek, L., et al., Long-Term Experience with Different Types of Localization Systems in Skull-Base Surgery, Ear, Nose & Throat Surgery, Chapter 51 (1996) pp. 635-638.

Lavallee et al., "Computer Assisted Spine Surgery: A Technique for Accurate Transpedicular Screw Fixation Using CT Data and a 3-D Optical Localizer," TIMC, Faculte de Medecine de Grenoble (1995).

Lavallee, "VI Adaption de la Methodologie a Quelques Applications Cliniques," Chapitre VI, pp. 133-148.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Prestige Cervical Disc System Surgical Technique, 12 pgs.

Reinhardt, Hans. F., Neuronavigation: A Ten-Year Review, Neurosurgery (1996) pp. 329-341.

Sautot, "Vissage Pediculaire Assiste Par Ordinateur," Sep. 20, 1994.

Simon, D.A., Accuracy Validation in Image-Guided Orthopaedic Surgery, Second Annual Intl. Symp. on Med. Rob. an Comp-Assisted surgery, MRCAS (1995) pp. 185-192.

The Laitinen Stereotactic System, E2-E6.

Viant et al., "A Computer Assisted Orthopaedic System for Distal Locking of Intramedullary Nails," Proc. of MediMEC '95, Bristol, 1995, pp. 86-91.

Butz et al. Pre- and Intra-operative Planning and Simulation of Percutaneous Tumor Ablation, Proceedings of the Third International Conference on Medical Image Computing and Computer-Assisted Intervention, p. 317-326, Oct. 11-14, 2000.

Wood et al. Technologies for Guidance of Radiofrequency Ablation in the Multimodality Interventional Suite of the Future. J Vasc Interv Radiol. Jan. 2007; 18(1 Pt 1): 9-24. doi:1 0.1 016/j.jvir.2006.1 0.013.

"Advanced Drug Delivery: Technologies, Applications & Markets Jul. 2003, A Kalorama Information Market Intelligence Report." (Jul. 2003) Kalorama Information 432 sheets.

"Interventional Radiology Grand Rounds. Topic: Central Venous Access." Society of Interventional Radiology, (2004) 4 sheets.

Arndt, "Neopharm Investigators Present Final Results of Peritumoral vs. Intratumoral Infusion of IL13-PE38QQR from Phase1 Clinical Studies at the American Society of Clinical Oncology Meeting." NeoPharm. Biowire2k 4st Annual Meeting of the American Society of Clinical Oncology. Business Wire (May 17, 2005) www.businesswire.com/news/home/20050517005098/en/NeoPharm-Investigators-Pr accessed Jul. 27, 2011.

Beghetto, M.G., et al. Parenteral Nutrition as a Risk Factor for Central Venous Catheter-Related Infection. Journal of Parenteral and Enteral Nutrition 29(5): (Sep. 4, 2005) pp. 367-373. http://www.redorbit.com/news/health/229618/parenteral_nutrition_as_a_risk_factor_for_central_venous_catheter/ (accessed Jul. 27, 2011).

Finnis, Kirk W., et al., "Three-Dimensional Database of Subcortical Electrophysiology for Image-Guided Stereotactic Functional Neurosurgery," IEEE Transactions of Medical Imaging, vol. 22, No. 1 (Jan. 2003) pp. 93-104.

Flanigan, M. et al.. Peritoneal Catheters and Exit-Site Practices Toward Optimum Peritoneal Access: A Review of Current Developments. Peritoneal Dialysis International. (2005) vol. 25, pp. 132-139.

Fletcher, S.J., et al. "Editorial II. Safe placement of central venous catheters: where should the tip of the catheter lie?" Oxford Journals, British Journal of Anaesthesia (2000) vol. 85 Issue 2, August. pp. 188-191.

Hanas, M.D., Ragnar. "Indwelling_Catheters_for_Injections. How to Reduce Injection Anxiety. Insuflon." (Jun. 2003) Children with Diabetes. http://www.childrenwithdiabetes.com/d_06_311.htm web accessed Jul. 27, 2011.

Hayashi, Y., et al. "Optimal Placement of CVP Catheter in Paediatric Cardiac Patients." Canadian Journal of Anesthesia, (1995) 42:6 pp. 479-482.

Hodge, D. et al. "Diagnosis, prevention, and management of catheter related bloodstream infection during long term parenteral nutrition." Arch. Dis. Child. Fetal Neonatal Ed. (2002) vol. 87 pp. F21-F24.

Hoenecke, Heinz, R., et al. "Continuous Local Anesthetic Infiltration," Case Report. Orthopedic Technology Review (Mar./Apr. 2002) vol. 3 No. 2. http://www.orthopedictechreview.com/issues/marapr02/case.htm. Said url is no longer valid. The article can be found using the Wayback Machine archive at: http://web.archive.org/web/20060315052636/http://www.orthopedictechreview.com/issues/marapr02/case.htm. Accessed and printed Aug. 11, 2011.

Kunwar, S., et al. "Peritumoral convection-enhanced delivery (CED) of IL13-PE38QQR (IL13PE): Results of multicenter phase 1 studies in recurrent High Grade Glioma (HGG)." Abstracts from the World Federation of Neuro-Oncology Second Quadrennial Meeting and Sixth Meeting of the European Association for Neuro-Oncology, Edinburgh, UK. (May 5-8, 2005) p. 311 Society for Neuro-Oncology.

Müller, M., et al. "Issues in Pharmacokinetics and Pharmacodynamics of Anti-Infective Agents: Distribution in Tissue." Antimicrobial Agents and Chemotherapy, MiniReview (2004) vol. 48, No. 5. pp. 1441-1453.

(56) References Cited

OTHER PUBLICATIONS

Renard, E., et. al. "Catheter Complications Associated with Implantable Systems for Peritoneal Insulin Delivery. An Analysis of Frequency, Predisposing Factors, and Obstructing Materials." Diabetes Care (Mar. 1995) vol. 18, No. 3. pp. 300-306.

Vande Walle, et al. "Use of Bicarbonate/Lactate Buffered Dialysate with Nighttime Cycler, Associated with a Daytime Dwell with Icodextrin, May Result in Alkalosis in Children." Advances in Peritoneal Dialysis (2004) vol. 20, pp. 222-225.

Vesely, T.M., "Central Venous Catheter Tip Position: A Continuing Controversy." J Vasc Interv Radiol (2003) vol. 14, No. 5. pp. 527-534.

Washburn, Kimberly, K, et al. "Surgical Technique for Peritoneal Dialysis Catheter Placement in the Pediatric Patient: A North American Survey." Advances in Peritoneal Dialysis (2004) vol. 20, pp. 218-221.

Zürcher, Matthias et al. "Colonization and Bloodstream Infection with Single-Versus Multi-Lumen Central Venous Catheters: A Quantitative Systematic Review." Anesthesia & Analgesia (2004) vol. 99, pp. 177-182.

* cited by examiner

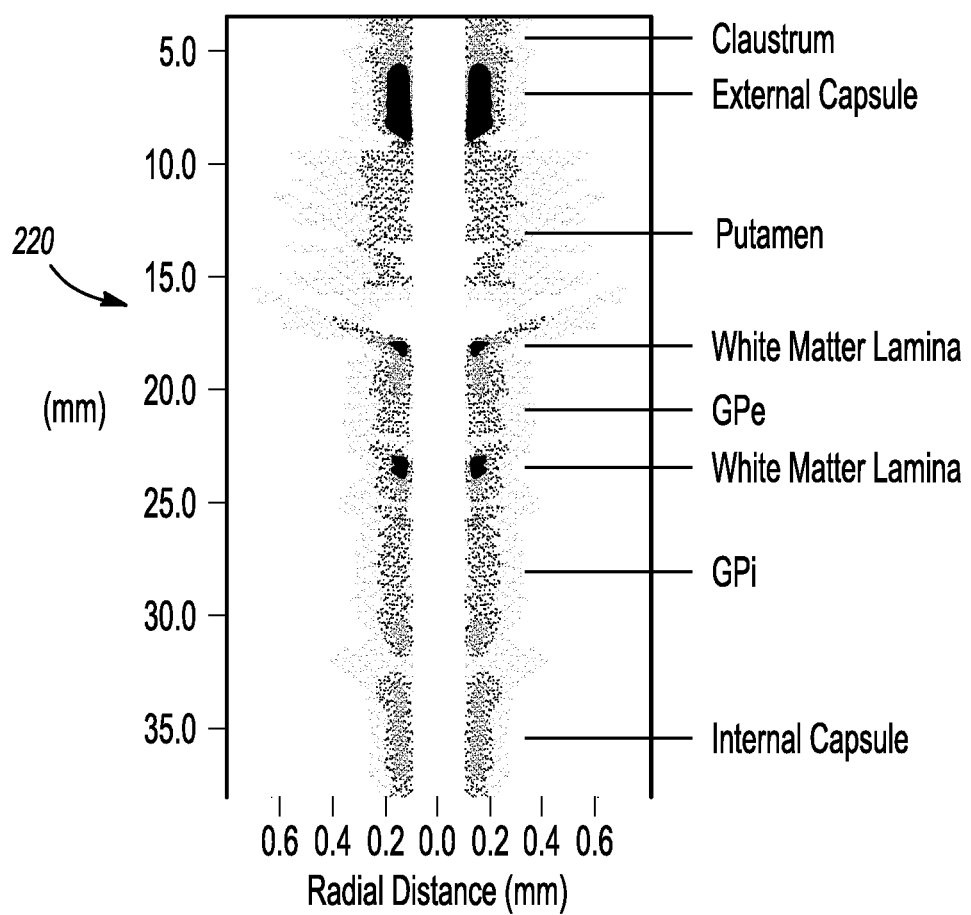
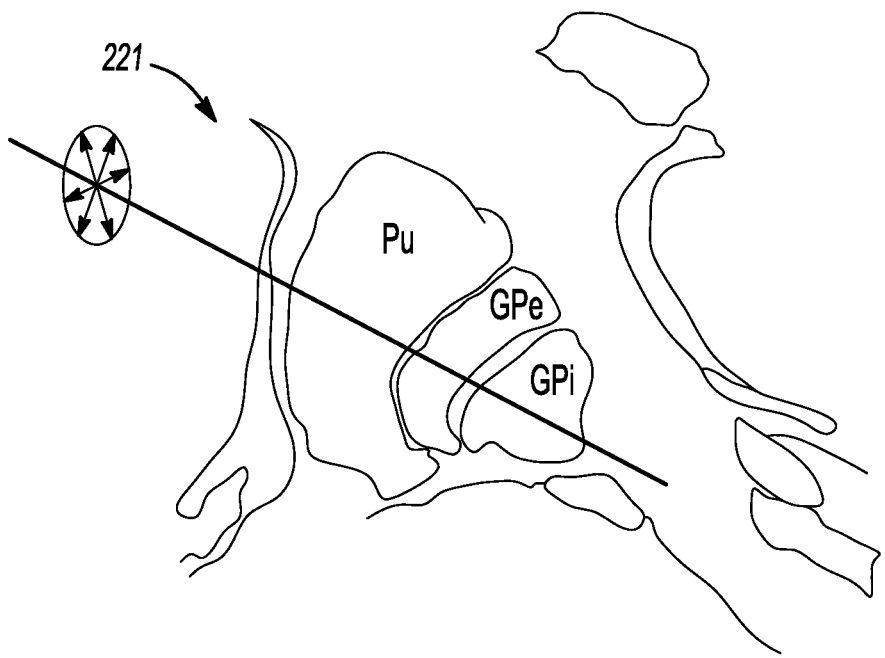
Fig-12

METHOD AND APPARATUS FOR OPTIMIZING A COMPUTER ASSISTED SURGICAL PROCEDURE

CROSS-REFERENCE TO RELATED APPLICATIONS

This application claims the benefit of U.S. Provisional Application No. 60/848,442, filed on Sep. 29, 2006. The disclosure of the above application is incorporated herein by reference.

FIELD

The present disclosure relates to a method and apparatus for performing a computer assisted surgical procedure, and particularly to a method and apparatus for optimizing a computer assisted surgical procedure.

BACKGROUND

The statements in this section merely provide background information related to the present disclosure and may not constitute prior art.

Various procedures can be performed on the anatomy of a patient to assist in providing various treatments to the patient. For example, an orthopedic procedure can include implanting a prosthesis or repairing an anatomical structure of a patient. Additional surgical procedures can include neurological procedures, cardiovascular procedures, and the like. Some of these exemplary procedures are generally selected to be performed in a small or minimally invasive manner. Some surgical procedures are performed in very surgically sensitive areas of the patient, such as in the brain or spinal area. In various procedures, therefore, an assistive system, such as an imaging or navigation system can be used to assist in a procedure. For example, a navigation system can be used to assist in illustrating a position of a device or instrument relative to a patient.

Although imaging systems to image portions of the anatomy and navigation systems are generally available, they may not provide multiple levels or types of information to the user. For example, an imaging device may generally only be able to provide one or two types of image data for use by a user. Nevertheless, providing several types of data for use during a single procedure may be desirable. For example, it may be desirable to provide a generally accepted map of a selected portion of the anatomy, such as the brain, for review during a procedure. It may also be desirable to illustrate a map of the anatomy relative to a patient specific image to assist in determining or verifying a location or target in the anatomy.

In addition, it may be desirable to provide a system that allows for integration of numerous types of systems. For example, it may be desirable to provide a system that allows for integration of both a navigation system, an imaging system, a data feedback system, and the like. Therefore, it is desirable to provide a system that allows for integration of several systems to allow for a synergistic approach to performing a selected surgical procedure. It is also desirable to provide an adaptive system that allows updating of static or database models to optimize various surgical procedures.

SUMMARY

Taught herein is a method and apparatus for providing an integrated adaptive system and approach to performing a surgical procedure. This system may be provided to obtain or display a selected type of data relating to a portion of the anatomy, and the system may allow for the synergy of several types of information for a single user. For example, image data of a particular patient, atlas information, instrument or recorder information, navigation information, archived or historical information, patient specific information and other appropriate types of information. All can be provided on or by a single system for use by a user during an operative procedure, after an operative procedure, or prior to an operative procedure.

In one example, various types of data can be provided to a user to plan a selected procedure. The plan and various types of data can be provided to a user during the actual procedure to assist navigating and assuring that the procedure is performed according to the plan. The data can also allow a user to perform a follow-up or programming of a device for a particular procedure. The data can assist the user in ensuring that an appropriate therapy is provided to a selected area of the anatomy, such as the brain. In addition, the various types of data can be used to post-operatively assist in refining various databases of data, such as atlases, including the anatomical and functional locations defined therein.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 12 is an illustration of physiological data according to various embodiments.

DETAILED DESCRIPTION

The following description is merely exemplary in nature and is not intended to limit the present disclosure, application, or uses.

Figure 1:
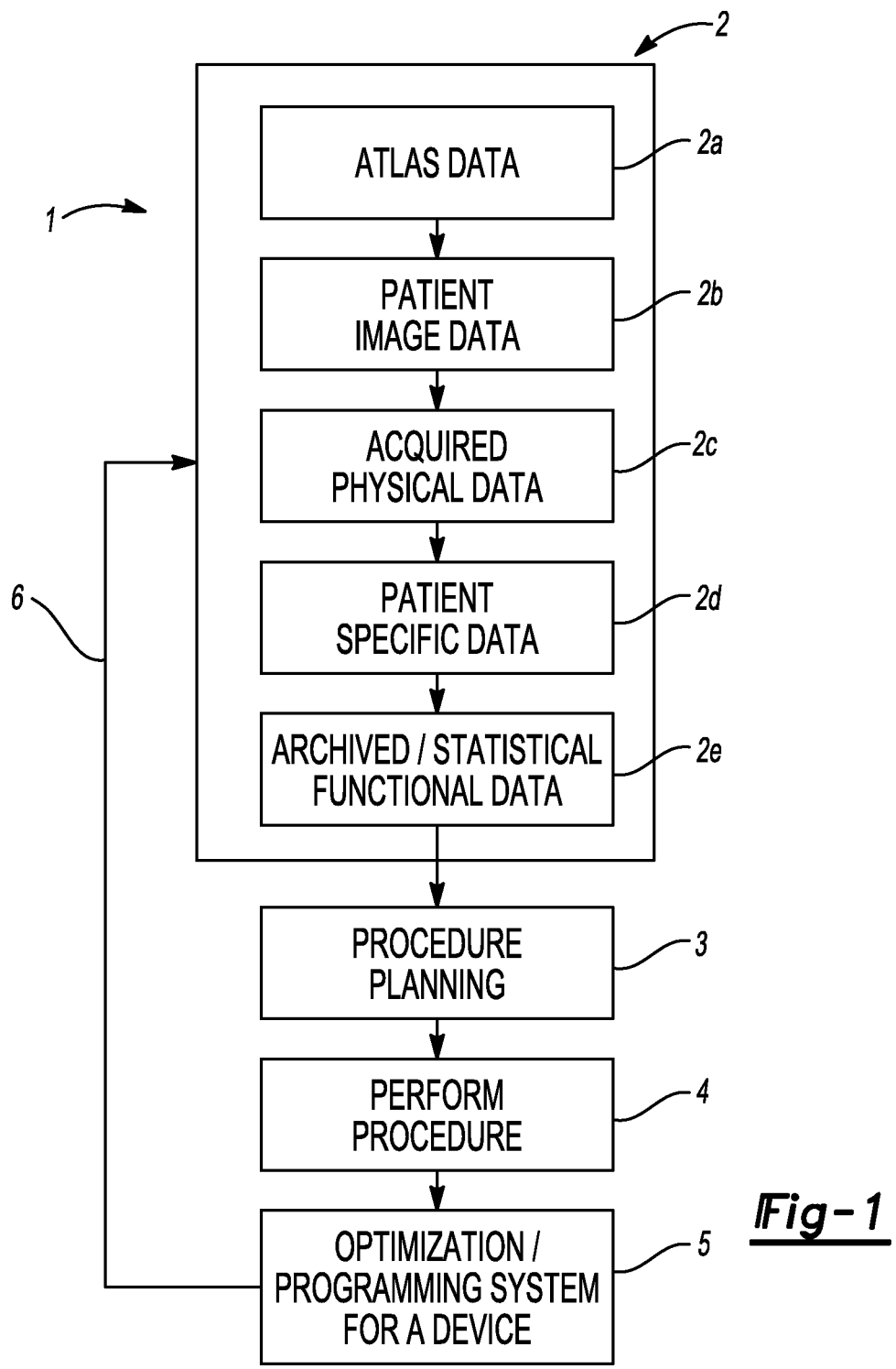
FIG. 1 is a schematic block diagram of an optimization system according to various embodiments.

With reference to FIG. 1, an optimization or synergistic system 1 is illustrated. The optimization system 1 can allow the provision of numerous types of data to be used or provided for planning a procedure, performing a procedure, optimizing a procedure, or assisting in updating or enhancing the data 2. The data 2 can include various types of data. Exemplary data can include atlas data 2a, patient image data 2b, acquired physiological data 2c, patient specific data 2d, and archived or statistical functional data 2e.

The various types of data 2 can be provided within the optimization system of 1 for use in various portions of the optimization procedure 1 The optimization system 1 can include a procedure planning 3, performing a procedure 4, or optimizing and programming a system 5, such as an implantable device. The various types of data 2 can be provided in any appropriate manner, such as visually, a list, a database, a computer accessible database, or the like.

The various types of data 2, although only exemplary and not intended to be an exhaustive list, can include atlas data 2a. The atlas data 2a can be any appropriate atlas data, such as a neurological atlas data, a cardiovascular atlas data, a musculature atlas data, skeletal atlas data, or the like. The atlas data can include three-dimensional atlas data 100 (FIG. 3) of selected portions of the anatomy. For example, atlas data can include three-dimensional atlas data of a neurological feature or structure, such as the sub-thalamic nucleus, various ventricles, and the like. Atlas data can also include two-dimensional atlas data 102 (FIG. 4) of portions of the anatomy, such as neurological portions. Other atlas data can also include the various boundaries of anatomical or functional features, locations of various anatomical or functional features, or any appropriate atlas data. Generally, the atlas data can be understood to be a well defined image data of a single or multiple patients. Generally accepted locations of functional or anatomical locations in an anatomy can be provided in the atlas data. The atlas data, as discussed further herein, can then be used to determine various functional or anatomical locations within an image data of a particular patient.

The data 2 provided within the optimization system 1 can also include the patient specific image data 2b. The patient specific image data 2b can be acquired in any appropriate manner, including those discussed further herein. The acquired image data can include magnetic resonance imaging data, diffusion tensor image data, optical coherence tomography image data, x-ray image data, or any appropriate image data. The patient image data can be acquired at any appropriate time, such as pre-operatively, intra-operatively or post-operatively. Also, as discussed further herein, the patient image data 2b can be registered to the atlas data 2a for use by a user within the optimization system 1. The atlas data 2a can be fitted to the image data of the patient 2b in any appropriate manner, also discussed further herein.

Also, other types of exemplary patient data that can be acquired, can include physiological data 2c. The physiological data 2c can be any appropriate type of data, such as electrical signal data recorded with a micro-electrode recorder (MER). Micro-electrode recording is understood by one skilled in the art and can be used to precisely pin point or locate various portions of the anatomy. For example, the MER can be used to determine the electrical signal relative to a single neuron or to a group of neurons. Further, the MER can be moved through the neurological tissue to determine differences between selected regions of a patient. The acquired physiological data, however, can also include any appropriate type of data, such as optical coherence tomography data 220 (see FIG. 12), temperature data, hydraulic data, or the like. The acquired physiological data can also be used with or superimposed on various types of patient specific data, such as the patient image data 2b. The acquired physiological data 2c can also be used to assist in an appropriate registration, re-registration or superimposing of the atlas data 2a onto the patient image data 2b.

In addition, various patient specific data in block 2d can also be provided. The patient specific data 2d can also include data, such as prior procedures, physical issues with the particular patient 14, or any appropriate patient specific data. The patient specific data 2d can also include a particular geometry or the patient, known locations of portions of the anatomy of the patient, and the like. Patient specific data 2d can also include functional data of the patient. Also, patient specific data can include function data acquired during a particular procedure. Functional data can include microelectrode recording data, pressure data, gating data, etc. Functional data, according to various embodiments, can be obtained with a microelectrode recorder, a scope, a catheter, or any other appropriate instrument.

In addition, as discussed above, the data 2 can include various archived or multiple procedural data portions or data sets 2e. Although various portions of the data can be integrated into the atlas data 2a, an additional database of data can include the archived or statistical functional data 2e. The archived and statistical functional data 2e can include data obtained during the performance of the procedure in block 4 or during the optimization and programming of the device, which can be implanted in the patient 14 in block 5. Archived or statistical functional data 2e can also include functional data of a group or previous patients. Functional data can include microelectrode recording data, pressure data, gating data, etc. The archived functional data can be used to augment data base data, including an atlas or other appropriate data. Therefore, the data in block 2 can include both data relating to the particular patient and to historical data that can assist in optimizing static data, such as atlas data, to a particular patient.

Figure 11:
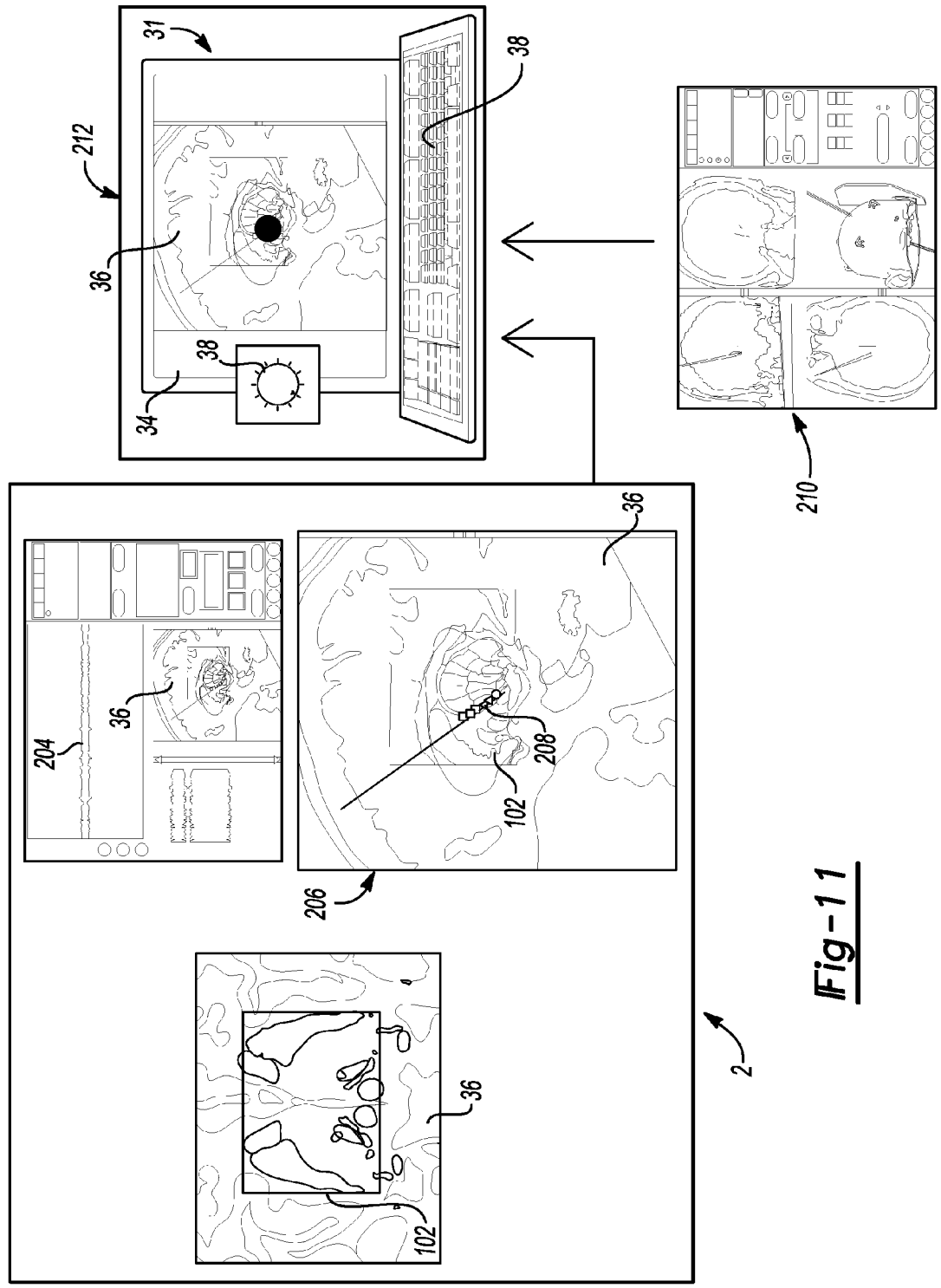
FIG. 11 is a block diagram graphical representation of an optimization system.

It will be understood that the system 1, as illustrated in FIG. 11, can include a substantially graphical interface that allows for both representation of the static and archived data and for manipulation of the data. Further, the archived data can be provided in a graphical manner relative to the patient specific data for illustration and reference during a particular procedure.

The data 2 can be provided to any appropriate procedure planning system 3. As discussed further herein, the data 2 can also be provided to an optimization or programming system for a device 5. The data 2 can be used in the procedure planning 3 or in the optimization programming system 5 to enhance or optimize a procedure on a particular patient. For example, the procedure planning block 3 can use the data 2 to assist in pre-selecting a target for a therapy, selecting a trajectory to reach the target for therapy, determining an appropriate amount of therapy, determining an appropriate type of therapy, or other appropriate pre-surgical planning information.

The data 2 can be provided, generally, in a database for access by a system or user. As discussed further herein, a workstation including a processor or any appropriate processor can execute instructions relating to the data base of the data 2. The database of the data 2 can be stored on a memory system for access by the processor. Thus, the data 2 can be accessed for use during a procedure, as discussed herein.

Also, as discussed further herein, a feedback 6 can allow the database of the data 2 to be augmented or updated. The database data 2 can be augmented or updated for use in multiple procedures or only in a current procedure. In this way, the data 2 in the database can be used in one or multiple procedures and accessed by multiple users. Thus, the data 2 can be used to optimize or assist in several procedures and updated and improved over time.

The data 2 in the database, can be accessed for use in a procedure. The data 2 in the database can be stored on a local memory system or accessed via a communications network. This can allow a centralized storage and access of the data 2 to efficiently update and augment the data 2 with numerous procedure data.

In planning a procedure, the patient image data 2b can be further refined with the acquired physiological data 2c or other patient specific information 2d. This can assist determining the location of the various anatomical or functional locations. Further, the data 2 can also include specific inputs or database inputs of the effective therapies on selected portions of the anatomy. For example, known effects of electrical stimulation, material delivery, or the like can be provided to assist in planning a procedure, including the amounts or type of therapy to be provided to a selected target or region.

Also, as discussed herein and illustrated in FIGS. 8-10B, various types of data can be used to illustrate the affect on the anatomy during a programming in the optimization of programming in block 5. However, this data can also be used pre-operatively, when illustrated relative to a selected location, such as a target location, to illustrate a possible affect of a therapy to be provided at the selected location. Therefore, the image data, atlas data, and the other database data can be used to plan a procedure. For example, an icon representing the implanted probe can be positioned on the image data of the patient and an icon representing an area affected by the therapy can be displayed relative to the probe. Planning the procedure can be used to select an optimal location, an optimal therapy based upon the optimal location, an optimal trajectory to attempt to reach the application, and the like. The instrument that is implanted can include a plurality of instruments, such as a plurality of DBS leads. Each of the instruments can be activated or used separately or together to provide a therapy.

The procedure planned in block 3 can also be performed in block 4 with the assistance of the data 2. As discussed herein, a device or instrument can be navigated relative to a patient, based upon the planned procedure from block 3, which is based upon the data from block 2. The navigation can be substantially imageless or with images to assist in ensuring that an appropriate location of the instrument or device is reached. Further, the data can be used to illustrate the type of therapy being provided and the effect of the therapy being provided to the patient. Also, various imaging techniques can be used to intraoperatively verify positioning of a selected device to ensure that the plan from the procedure planning of block 3 has been achieved.

As understood by one skilled in the art, various types of devices may be programmed or optimized once they are implanted or positioned relative to a patient. For example, a deep brain stimulator (DBS) probe can be implanted into the brain and can be programmed over time to achieve an optimal result. It will be understood, however, that various types of implantable devices can also be employed to provide any appropriate type of therapy, such as a pacing lead, a drug delivery therapy, a pharmaceutical delivery, a cell or gene delivery therapy, or any appropriate type of therapy and delivery. Therefore, the optimization and programming system in block 5 can use the data from block 2 to assist in determining the appropriate type of programming that should be provided. For example, also discussed further herein, an appropriate voltage and pulse width can be programmed for an appropriate lead to stimulate a selected portion of the anatomy. The data from block 2 can be used to assist in determining the appropriate voltage, the appropriate pulse width, and the appropriate lead to be activated.

Also, the optimization and programming system for the device 5 can be used to assist in creating or augmenting the data in block 2, via feedback 6. For example, when providing a selected voltage, pulse width, and the like achieves the selected result or achieves a particular result, the data from block 2 can be augmented or changed based upon the observed result. The optimal location or optimal initial voltage, pulse width, therapy delivery, or the like can be input for retrieval when planning a procedure 3 from the data block 2.

Figure 2:
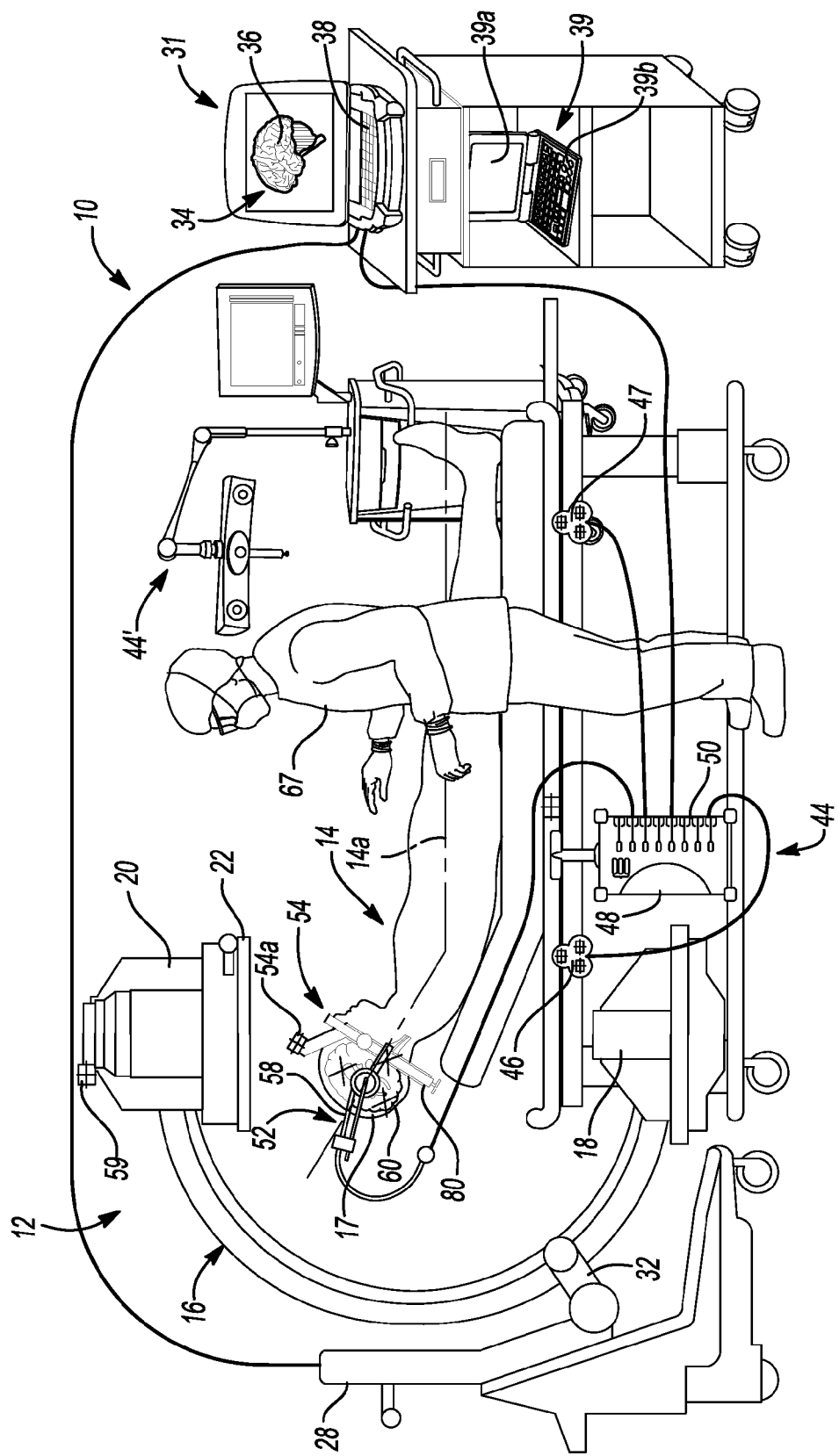
FIG. 2 is an environmental view of a navigation system according to various embodiments.

The procedure can be planned or performed with any appropriate system, which can include a navigation system 10 (FIG. 2). The navigation system 10 can be used by any appropriate individual, such as a user to assist in both planning and performing a procedure. Nevertheless, the data 2 can be used and processed by a user or an electronic processor to assist in planning or performing a procedure.

Figure 2A:
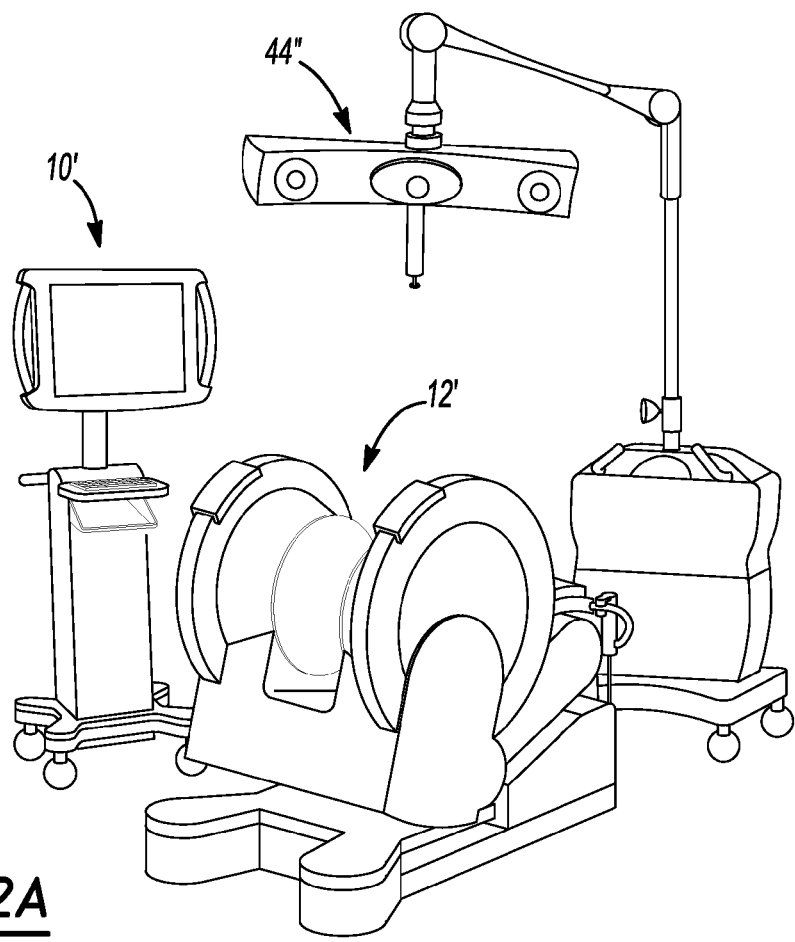
FIG. 2A is an environmental view of a navigation system according to various embodiments.
Figure 2B:
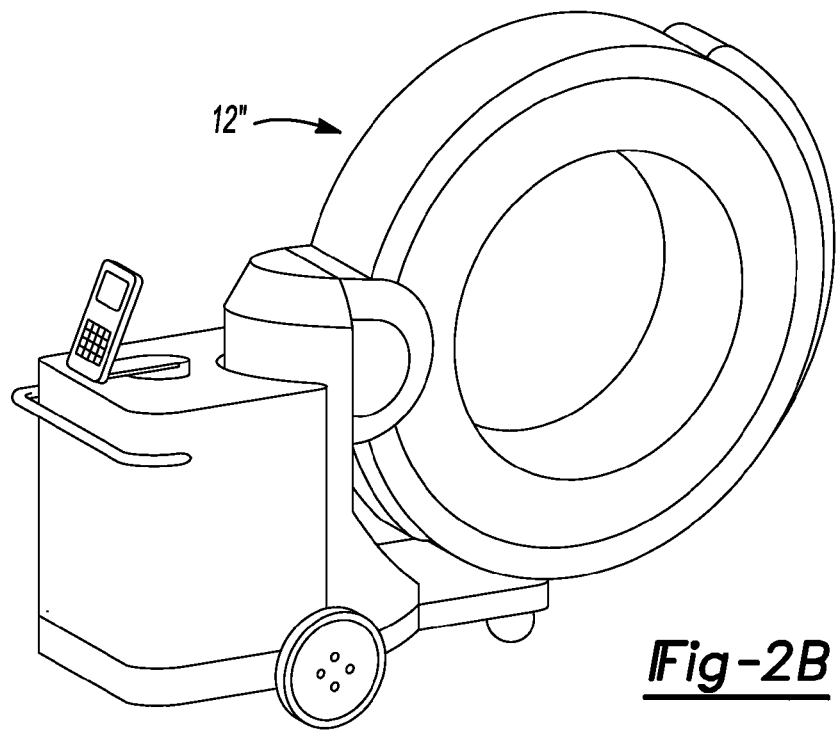
FIG. 2B is an environmental view of a navigation system according to various embodiments.

With reference to FIG. 2 the navigation system 10 that can be used for various procedures in relation to the optimized therapy plan and system 1. The navigation system 10 can be used to track the location of a device, such as a delivery device, relative to a patient 14 to assist in the implementation of the plan in block 3, and discussed herein. It should be further noted that the navigation system 10 may be used to navigate or track other devices including: catheters, probes, needles, leads, implants, etc. Moreover, the navigated device may be used in any region of the body. The navigation system 10 and the various devices may be used in any appropriate procedure, such as one that is generally minimally invasive, arthroscopic, percutaneous, stereotactic, or an open procedure. Although an exemplary navigation system 10 including an imaging system 12 are discussed herein, one skilled in the art will understand that the disclosure is merely for clarity of the present discussion and any appropriate imaging system, navigation system, patient specific data, and non-patient specific data can be used. For example, the imaging system can include an MRI imaging system 12' (FIG. 2A) or an O-arm imaging system 12" (FIG. 2B).

The navigation system 10 can include the optional imaging device 12 that is used to acquire pre-, intra-, or post-operative or real-time image data of a patient 14. The image data acquired with the imaging device 12 can be used as part of the patient specific information in block 2. Alternatively various imageless systems can be used or images from atlas models can be used to produce patient images, such as those disclosed in U.S. patent application Ser. No. 10/687,539, filed Oct. 16, 2003, entitled "METHOD AND APPARATUS FOR SURGICAL NAVIGATION OF A MULTIPLE PIECE CONSTRUCT FOR IMPLANTATION", incorporated herein by reference. The optional imaging device 12 is, for example, a fluoroscopic X-ray imaging device that may be configured as a C-arm 16 having an X-ray source 18, an X-ray receiving section 20, an optional calibration and tracking target 22 and optional radiation sensors 24. The calibration and tracking target 22 includes calibration markers (not illustrated). Image data may also be acquired using other imaging devices, such as those discussed above and herein.

An optional imaging device controller 28 may control the imaging device 12, such as the C-arm 16, which can capture the x-ray images received at the receiving section 20 and store the images for later use. The controller 28 may also be separate from the C-arm 16 and can be part of or incorporated into a work station 31. The controller 28 can control the rotation of the C-arm 16. For example, the C-arm 16 can move in the direction of arrow 30 or rotate about a longitudinal axis 14a of the patient 14, allowing anterior or lateral views of the patient 14 to be imaged. Each of these movements involves rotation about a mechanical axis 32 of the C-arm 16. The movements of the imaging device 12, such as the C-arm 16 can be tracked with a tracking device 59.

In the example of FIG. 2, the longitudinal axis 14a of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray device that may be used as the optional imaging device 12 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, intraoperative O-arms, etc.

In operation, the C-arm 16 generates X-rays from the—X-ray source 18 that propagate through the patient 14 and calibration and/or tracking target 22, into the X-ray receiving section 20. This allows direct visualization of the patient 14 and radio-opaque instruments in the cone of X-rays. It will be understood that the tracking target or device need not include a calibration portion. The receiving section 20 generates image data representing the intensities of the received X-rays. Typically, the receiving section 20 includes an image intensifier that first converts the X-rays to visible light and a charge coupled device (CCD) video camera that converts the visible light into digital image data. Receiving section 20 may also be a digital device that converts X-rays directly to digital image data for forming images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used at all for various procedures. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images that may be taken by the imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg or cranium and brain may be appended together to provide a full view or complete set of image data of the leg or brain that can be later used to follow contrast agent, such as Bolus or therapy tracking.

The image data can then be forwarded from the C-arm controller 28 to a navigation computer and/or processor controller or work station 31 having a display 34 to display image data 36 and a user interface 38. The work station 31 can also include or be connected to an image processor, navigation processor, and memory to hold instruction and data. The work station 31 can include an optimization processor, which includes the system 1, as discussed herein, or a separate optimization processor system 39 can be included. The optimization processor system 39 can also include a display 39a and a user input 39b. It will also be understood that the image data is not necessarily first retained in the controller 28, but may also be directly transmitted to the workstation 31, which can also include an image processor, navigation processor, memory, etc. Moreover, processing for the navigation system and optimization can all be done with a single or multiple processors.

The work station 31 or optimization processor 39 provides facilities for displaying the image data 36 as an image on the display 34, saving, digitally manipulating, or printing a hard copy image of the received image data. The user interface 38, which may be a keyboard, mouse, touch pen, touch screen or other suitable device, allows a physician or user 67 to provide inputs to control the imaging device 12, via the C-arm controller 28, or adjust the display settings of the display 34. The work station 31 may also direct the C-arm controller 28 to adjust the rotational axis 32 of the C-arm 16 to obtain various two-dimensional images along different planes in order to generate representative two-dimensional and three-dimensional images.

The optimization processor 39 can be provided in any appropriate format, such as a substantially portable format. The optimization processor 39 can be used in any appropriate portion of the optimization process or system 1. For example, the optimization processor 39 can be separate from the navigation processor to allow for planning of the procedure, programming of the device in step 5, or any appropriate portion.

Various calibration techniques can be used to calibrate the imaging device 12. Intrinsic calibration, which is the process of correcting image distortion in a received image and establishing the projective transformation for that image, involves placing the calibration markers in the path of the x-ray, where the calibration markers are opaque or semi-opaque to the x-rays. A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the optional imaging device 12 is shown in FIG. 2, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference), intra-vascular ultrasound (IVUS), intra-operative CT, single photo emission computed tomography (SPECT), planar gamma scintigraphy (PGS). Addition imaging systems include intraoperative MRI systems 12. (FIG. 2A), such as the PoleStar® MRI system sold by Medtronic, Inc. Further systems include the O-Arm™ imaging system 12 (FIG. 2B) sold by Breakaway Imaging, LLC. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 12, as shown in FIG. 2, provides a virtual bi-plane image using a single-head C-arm fluoroscope as the optional imaging device 12 by simply rotating the C-arm 16 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, or probe introduced and advanced in the patient 14, may be superimposed in more than one view on display 34 allowing simulated bi-plane or even multi-plane views, including two and three-dimensional views.

4D image information can be used with the navigation system 10 as well. For example, the user 67 can use the physiologic signal 2C, which can include Heart Rate (EKG), Breath Rate (Breath Gating) and combine this data with image data 2b acquired during the phases of the physiologic signal to represent the anatomy at various stages of the physiologic cycle. For example, the brain pulses (and therefore moves) with each heartbeat. Images can be acquired to create a 4D map of the brain, onto which the atlas data 2a and representations of the instrument can be projected. This 4D data set can be matched and co-registered with the physiologic signal (EKG) to represent a compensated image within the system. The image data registered with the 4D information can show the brain (or anatomy of interest) moving during the cardiac or breath cycle. This movement can be displayed on the display 34 as the image data 36.

Likewise, other imaging modalities can be used to gather the 4D dataset to which pre-operative 2D and 3D data can be matched. One need not necessarily acquire multiple 2D or 3D images during the physiologic cycle of interest (breath or heart beat). Ultrasound imaging or other 4D imaging modalities can be used to create an image data that allows for a singular static pre-operative image to be matched via image-fusion techniques and/or matching algorithms that are non-linear to match the distortion of anatomy based on the movements during the physiologic cycle. The combination of a the dynamic reference frame 54 and 4D registration techniques can help compensate for anatomic distortions during movements of the anatomy associated with normal physiologic processes.

With continuing reference to FIG. 2, the navigation system 10 can further include an electromagnetic navigation or tracking system 44 that includes a localizer, such as a coil array 46 and/or second coil array 47, the coil array controller 48, a navigation probe interface 50, a device 52 (e.g. catheter, needle, or instruments, as discussed herein) and a dynamic reference frame 54. Other tracking systems can include optical tracking systems 44', 44" exemplary optical tracking systems include the StealthStation® Treon® and the StealthStation® Tria® both sold by Medtronic Navigation, Inc. The dynamic reference frame 54 can include a dynamic reference frame holder 80 and a removable tracking device 54a. Alternatively, the dynamic reference frame 54 can include a tracking device 54a that is formed integrally with the dynamic reference frame holder 80.

The tracking device 54a or any appropriate tracking device as discussed herein, can include both a sensor, a transmitter, or combinations thereof. Further, the tracking devices can be wired or wireless to provide a signal or emitter or receive a signal from a system. Nevertheless, the tracking device can include an electromagnetic coil to sense a field produced by the localizing array 46 or 47 or reflectors that can reflect a signal to be received by the optical localizer 44', 44". Nevertheless, one will understand that the tracking device can receive a signal, transmit a signal, or combinations thereof to provide information to the navigation system 10 to determine a location of the tracking device 54a, 58. The navigation system can then determine a position of the instrument or tracking device to allow for navigation relative to the patient and patient space.

The coil arrays 46, 47 may also be supplemented or replaced with a mobile localizer. The mobile localizer may be one such as that described in U.S. patent application Ser. No. 10/941,782, filed Sep. 15, 2004, and entitled "METHOD AND APPARATUS FOR SURGICAL NAVIGATION", herein incorporated by reference. As is understood the localizer array can transmit signals that are received by the tracking device 54a, 58. The tracking device 58 can then transmit or receive signals based upon the transmitted or received signals from or to the array.

Other tracking systems include acoustic, radiation, radar, infrared, etc. The optical localizer can transmit and receive, or combinations thereof. An optical tracking device can be interconnected with the instrument 52, or other portions such as the dynamic reference frame 54. As is generally known the optical tracking device 58a can reflect, transmit or receive an optical signal to the optical localizer 44' that can be used in the navigation system 10 to navigate or track various elements. Therefore, one skilled in the art will understand, that the tracking devices 54a, 58, and 59 can be any appropriate tracking device to work with any one or multiple tracking systems.

Further included in the navigation system 10 may be an isolator circuit or assembly. The isolator circuit or assembly may be included in a transmission line to interrupt a line carrying a signal or a voltage to the navigation probe interface 50. Alternatively, the isolator circuit included in the isolator box may be included in the navigation probe interface 50, the device 52, the dynamic reference frame 54, the transmission lines coupling the devices, or any other appropriate location. The isolator assembly is operable to isolate any of the instruments or patient coincidence instruments or portions that are in contact with the patient should an undesirable electrical surge or voltage take place.

It should further be noted that the entire tracking system 44 or parts of the tracking system 44 may be incorporated into the imaging device 12, including the work station 31, radiation sensors 24 and optimization processor 39. Incorporating the tracking system 44 may provide an integrated imaging and tracking system. This can be particularly useful in creating a fiducial-less system. Any combination of these components may also be incorporated into the imaging system 12, which again can include a fluoroscopic C-arm imaging device or any other appropriate imaging device.

The coil array 46 can include a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 46 is controlled or driven by the coil array controller 48. The coil array controller 48 drives each coil in the coil array 46 in a time division multiplex or a frequency division multiplex manner. In this regard, each coil may be driven separately at a distinct time or all of the coils may be driven simultaneously with each being driven by a different frequency.

Upon driving the coils in the coil array 46 with the coil array controller 48, electromagnetic fields are generated within the patient 14 in the area where the medical procedure is being performed, which is again sometimes referred to as patient space. The electromagnetic fields generated in the patient space induce currents in the tracking device 54a, 58 positioned on or in the device 52. These induced signals from the tracking device 58 are delivered to the navigation probe interface 50 and subsequently forwarded to the coil array controller 48. The navigation probe interface 50 can also include amplifiers, filters and buffers to directly interface with the tracking device 58 in the device 52. Alternatively, the tracking device 58, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

Various portions of the navigation system 10, such as the device 52, the dynamic reference frame (DRF) 54, the instrument 52, are equipped with at least one, and generally multiple, EM or other tracking devices 58, that may also be referred to as localization sensors. The EM tracking devices 58 can include one or more coils that are operable with the EM localizer array 46 or 47. An alternative tracking device may include an optical sensor, and may be used in addition to or in place of the electromagnetic sensor 58. The optical sensor may work with the optional optical array 44'. One skilled in the art will understand, however, that any appropriate tracking device can be used in the navigation system 10. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

In brief, the EM tracking device 58 on the device 52 can be in a handle or inserter that interconnects with an attachment and may assist in placing an implant or in driving a portion. The device 52 can include a graspable or manipulable portion at a proximal end and the tracking device 58 may be fixed near the manipulable portion of the device 52 or at a distal working end, as discussed herein. The tracking device 58 can include an electromagnetic sensor to sense the electromagnetic field generated by the coil array 46 that can induce a current in the electromagnetic device 58. Alternatively, the tracking sensor 54a, 58 can be driven (i.e., like the coil array above) and the tracking array 46, 46a can receive a signal produced by the tracking device 54a, 58.

The dynamic reference frame 54 may be fixed to the patient 14 adjacent to the region being navigated so that any movement of the patient 14 is detected as relative motion between the coil array 46 and the dynamic reference frame 54. The dynamic reference frame 54 can be interconnected with the patient in any appropriate manner, including those discussed herein. This relative motion is forwarded to the coil array controller 48, which updates registration correlation and maintains accurate navigation, further discussed herein. The dynamic reference frame 54 may be any appropriate tracking sensor used as the dynamic reference frame 54 in the navigation system 10. Therefore the dynamic reference frame 54 may also be optical, acoustic, etc. If the dynamic reference frame 54 is electromagnetic it can be configured as a pair of orthogonally oriented coils, each having the same center or may be configured in any other non-coaxial or co-axial coil configurations.

Briefly, the navigation system 10 operates as follows. The navigation system 10 creates a translation map between all points in the image data generated from the imaging device 12 which can include external and internal portions, and the corresponding points in the patient's anatomy in patient space. After this map is established, whenever the tracked device 52 is used the work station 31 in combination with the coil array controller 48 and the C-arm controller 28 uses the translation map to identify the corresponding point on the pre-acquired image or atlas model, which is displayed on display 34. This identification is known as navigation or localization. An icon representing the localized point or instruments is shown on the display 34 within several two-dimensional image planes, as well as on three and four dimensional images and models.

To enable navigation, the navigation system 10 must be able to detect both the position of the patient's anatomy and the position of the instrument 52 or attachment member (e.g. tracking device 58) attached to the instrument 52. Knowing the location of these two items allows the navigation system 10 to compute and display the position of the instrument 52 or any portion thereof in relation to the patient 14. The tracking system 44 is employed to track the instrument 52 and the anatomy simultaneously.

The tracking system 44, if it is using an electromagnetic tracking assembly, essentially works by positioning the coil array 46 adjacent to the patient space to generate a magnetic field, which can be low energy, and generally referred to as a navigation field. Because every point in the navigation field or patient space is associated with a unique field strength, the electromagnetic tracking system 44 can determine the position of the instrument 52 by measuring the field strength at the tracking device 58 location. The dynamic reference frame 54 is fixed to the patient 14 to identify the location of the patient in the navigation field. The electromagnetic tracking system 44 continuously recomputes the relative position of the dynamic reference frame 54 and the instrument 52 during localization and relates this spatial information to patient registration data to enable image guidance of the device 52 within and/or relative to the patient 14.

Patient registration is the process of determining how to correlate the position of the instrument 52 relative to the patient 14 to the position on the diagnostic or pre-acquired images. To register the patient 14, a physician or user 67 may use point registration by selecting and storing particular points (e.g. fiducial points 60) from the pre-acquired images and then touching the corresponding points on the patient's anatomy with the pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial markers or landmarks 60, such as anatomical landmarks. Again, the landmarks or fiducial points are identifiable on the images and identifiable and accessible on the patient 14. The landmarks 60 can be artificial landmarks 60 that are positioned on the patient 14 or anatomical landmarks that can be easily identified in the image data. The artificial landmarks, such as the fiducial markers 60, can also form part of the dynamic reference frame 54, such as those disclosed in U.S. Pat. No. 6,381,485, entitled "Registration of Human Anatomy Integrated for Electromagnetic Localization," issued Apr. 30, 2002, herein incorporated by reference.

The system 10 may also perform registration using anatomic surface information or path information as is known in the art (and may be referred to as auto-registration). The system 10 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, entitled "Method and Apparatus for Performing 2D to 3D Registration" filed on Aug. 20, 2003, hereby incorporated by reference.

Also as discussed herein, a substantially fiducial-less registration system can be provided, particularly if the imaging device 12 and the tracking system 44 are substantially integrated. Therefore, the tracking system 44 would generally know the position of the imaging device 12 relative to the patient 14 and fiducials may not be required to create registration. Nevertheless, it will be understood that any appropriate type of registration system can be provided for the navigation system 10.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Alternatively the patient 14 may be held immobile once the registration has occurred, such as with a head frame. Therefore, if the navigation system 10 did not track the position of the patient 14 or area of the anatomy, any patient movement after image acquisition would result in inaccurate navigation within that image. The dynamic reference frame 54 allows the electromagnetic tracking system 44 to register and track the anatomy. Because the dynamic reference frame 54 is rigidly fixed to the patient 14, any movement of the anatomy or the coil array 46 is detected as the relative motion between the coil array 46 and the dynamic reference frame 54. This relative motion is communicated to the coil array controller 48, via the navigation probe interface 50, which updates the registration correlation to thereby maintain accurate navigation.

The navigation system 10 can be used according to any appropriate method or system. For example, pre-acquired images, atlas or 3D models may be registered relative to the patient and patient space, as discussed further herein. Generally, the navigation system allows the images on the display 34 to be registered and accurately display the real time location of the various instruments and other appropriate items, such as the trackable pointer. In addition, the pointer may be used to register the patient space to the pre-acquired images or the atlas or 3D models. In addition, the dynamic reference frame 54 may be used to ensure that any planned or unplanned movement of the patient or the receiver array 46 is determined and used to correct the image on the display 36.

With additional reference to FIG. 2, the dynamic reference frame 54 can be affixed to any appropriate portion of the patient 14, and can be used to register the patient to the image data, as discussed above. For example, when a procedure is being performed relative to a cranium 17, the dynamic reference frame 54 can be interconnected with the cranium 17. The dynamic reference frame 54 can be interconnected with the cranium 17 in any appropriate manner, such as those discussed herein according to various embodiments.

To obtain a maximum reference it can be selected to fix the dynamic reference frame 54 in each of at least 6 degrees of freedom. Thus, the dynamic reference frame 54 can be fixed relative to axial motion X, translational motion Y, rotational motion Z, yaw, pitch, and roll relative to the portion of the patient 14 to which it is attached. Any appropriate coordinate system can be used to describe the various degrees of freedom. Fixing the dynamic reference frame relative to the patient 14 in this manner can assist in maintaining maximum accuracy of the navigation system 10.

In addition the dynamic reference frame 54 can be affixed to the patient in such a manner that the tracking sensor portion thereof is immovable relative to the area of interest, such as the cranium 17. A head band may form a part of the dynamic reference from 54. Further, a stereotactic frame, as generally known in the art, can be attached to the head band. Such systems for tracking and performing procedures are disclosed in U.S. patent application Ser. No. 10/651,267, filed on Aug. 28, 2003, and incorporated herein by reference.

The instrument 52 can be a DBS probe, a MER device, a catheter, etc. and each can include at least one of the tracking devices, such as the tracking device 58. The tracking device 58 can be any appropriate tracking device and can be formed in any appropriate manner such as the catheters described in pending U.S. patent application Ser. No. 11/241,837, filed on Sep. 30, 2005, incorporated herein by reference.

The catheter 52 can include the tracking device 58 at any appropriate position, such as near a distal end of the catheter 52. By positioning the tracking device 58 near the distal end of the catheter 52 knowing or determining a precise location of the distal end can be efficient. Determining a position of the distal end of the catheter 52 can be used to achieve various results, such as determining a precise position of the distal end of the catheter 52, a precise movement of the distal end of the catheter 52. It will be understood that knowing a position and moving the catheter 52 in a precise manner can be useful for various purposes, including those discussed further herein. Likewise, the catheter 52 can be directable according to various mechanisms and such as directing or pulling wires, directing or pulling signals, or any appropriate mechanism generally known in the art.

The catheter 52 can be used for various mechanisms and methods, such as delivering a material to a selected portion of the patient 14, such as within the cranium 17. The material can be any appropriate material such as a bioactive material, a pharmacological material, a contrast agent. Instead of a material, a therapy such as electrical stimulation can be used with a deep brain stimulation probe (DBS). The DBS can be used to apply a voltage, a pulse width, etc. to a selected portion of the brain.

As mentioned briefly above, the display 34 can display any appropriate type of image data 36. For example, the image data 36 can include patient specific image data that can be acquired at any appropriate time. The image data can include magnetic resonance imaging data (MRI) that can provide structural anatomical image data of the patient 14. The image data can be displayed on the display 34 for use during a procedure by the user 67. The display on the display 34 can also include various atlas image data. Atlas image data can include two-dimensional image data sets, three-dimensional image data sets, and even four-dimensional image data sets that show the change of various anatomical structures over time.

Figure 3:
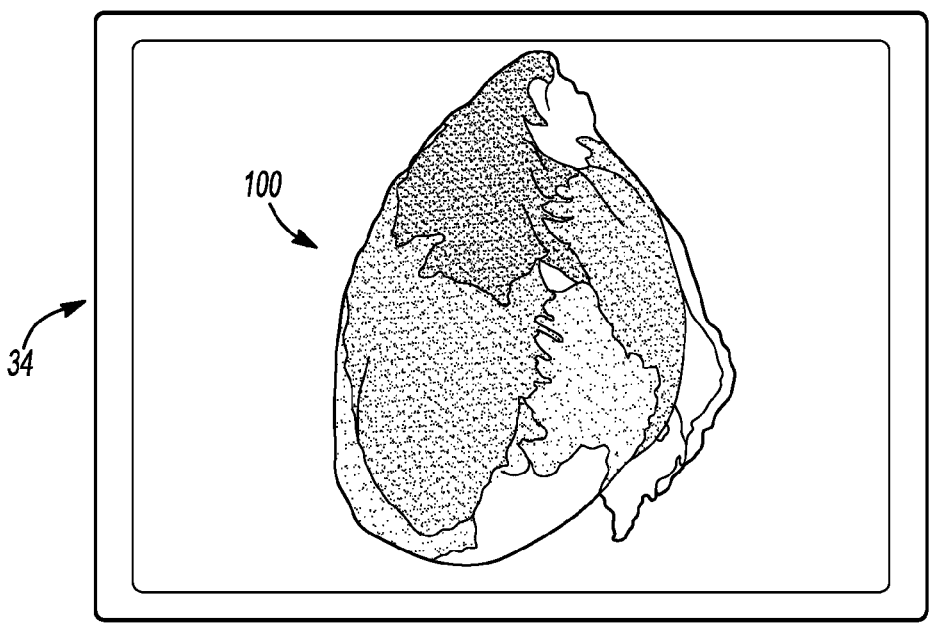
FIG. 3 is an illustration of three-dimensional atlas data according to various embodiments.

With reference to FIG. 3, a three-dimensional atlas data set 100 is illustrated for a neurological region. The neurological region illustrated in FIG. 3 can be any appropriate neurological region, such as a sub-thalamic nucleus, a cerebrum, or the like. In addition, the three-dimensional atlas 100 can be used to identify various regions of the anatomy of the patient 14 on the display 34. For example, the atlas image 100 can be registered to the image data 36 in any appropriate manner. For example, the atlas can be registered to the image data using generally known algorithms, registration or fiducial markers, and the like. Nevertheless, the 3-D atlas 100 can be used to identify or assist in identifying various landmarks within the image data 36 of the patient 14. Certain algorithms can include shape matching, space matching, or structure matching. Shape fitting algorithms can include least square fitting to match one image to another.

Figure 4:
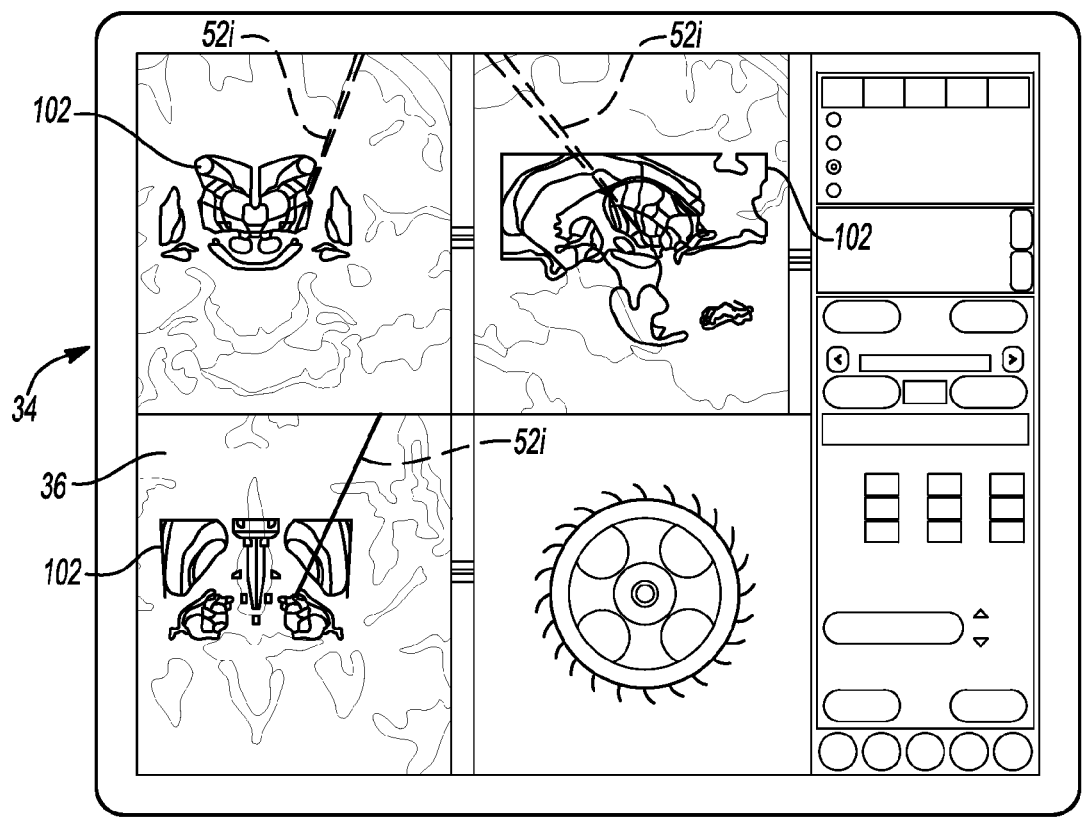
FIG. 4 is an illustration of image data and atlas data according to various embodiments.

With reference to FIG. 4, a 2-D atlas image data 102 can be overlaid on the image data 36 of the patient 14. The display 34 can include various regions that show the image data 36 of the patient 14 from a plurality or any appropriate perspectives. In addition, the display device 34 can display a position of the instrument 52 with an icon 52i. The icon 52i can illustrate a position of the instrument 52 relative to a selected portion of the anatomy, such as identified by the atlas 102 or any other appropriate procedure. The atlas 102 can also be registered to the image data 36 of the patient 14 according to various known techniques, including various automatic or manual registration techniques. The registration of the atlas data 102 to the image data 36 can assist in identifying various anatomical and functional landmarks or portions of the anatomy of the patient 14.

Figure 5:
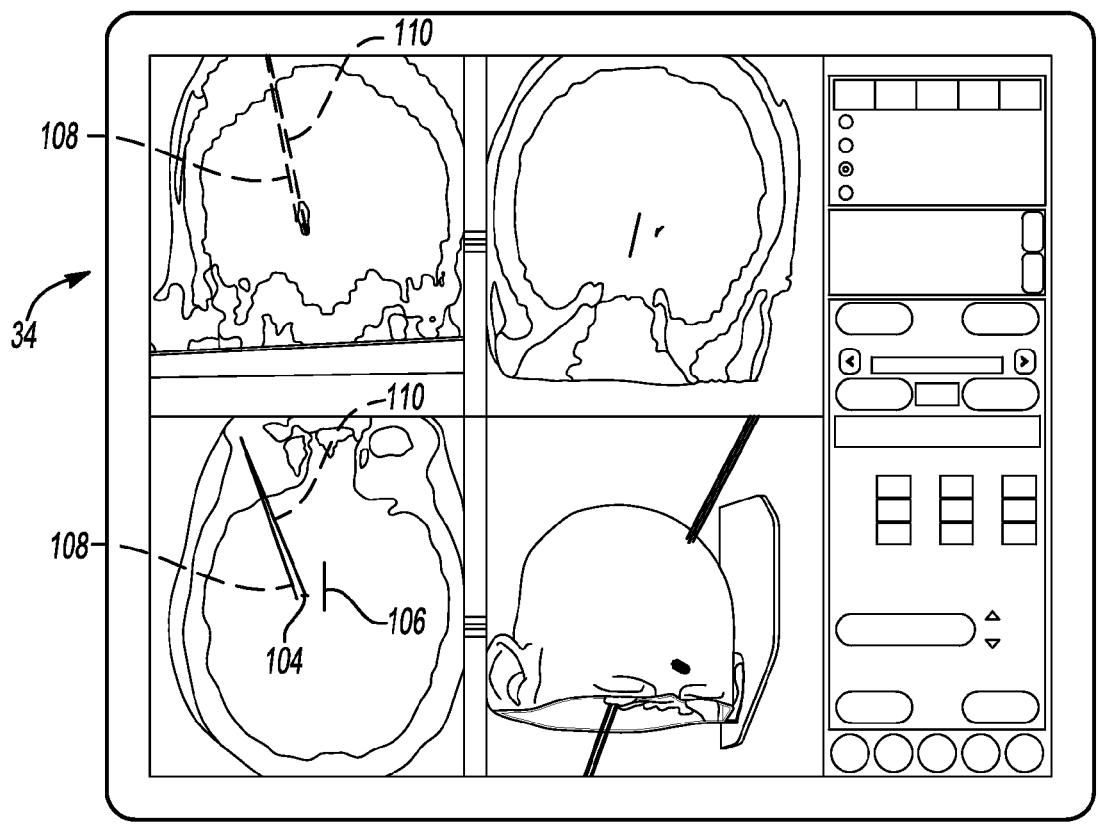
FIG. 5 is an illustration of image data and planning data according to various embodiments.

With reference to FIG. 5, the display 34 can be used to display various types of image data, including the image data 36 of the patient 14, and atlas image data relative thereto. The appropriate type of image data displayed on the display 34 can then be used to plan a selected procedure. The planning can occur substantially pre-operatively or intra-operatively. Nevertheless, various targets 104, 106 can be displayed on the display 34 as can various trajectories 108, 110. The targets 104, 106 and the trajectories 108, 110 can be displayed on the display 34 for selection by the user 67. It will be understood that the plan can be prepared at any appropriate time to assist in performing the procedure with the navigation system 10. Also, the plan can be created manually, automatically, or combinations thereof. The plan, including a target and trajectory, can then be selected manually, automatically, or combinations thereof.

The planning procedure can use the atlas data, and functional data, discussed further herein, to assist in determining the appropriate location of the targets 104, 106. In addition, the anatomical and functional features identified in the image data 36 can be used to assist in determining the appropriate trajectory 108, 110. Various aiming devices can also be tracked in addition to tracking the instrument 52, as discussed further herein. The identification of appropriate trajectories 108, 110 or the selection of one of many trajectories, such as the selected trajectories 108, 110 can be used to assist in positioning an appropriate aiming device or the instrument 52 during a procedure.

The planning information displayed on the display 34 can also be used post-operatively to determine whether the device, such as a deep brain stimulation probe, was implanted or positioned at an appropriate location, such as a planned location 104, 106. The planning information displayed on the display 34 can be compared to post-operative image data, such as a post-operative MRI of the patient 14, to assist in determining the success or the final positioning of the selected implant. In addition, the post-operative information can be used with the optimization/programming system for the device in block 5 to assist in ensuring that an appropriate lead, therapy, or the like is provided to the selected or target location. Therefore, the planning information on the display 34 can be used to assist in ensuring that an appropriate therapy is provided to the patient, as discussed further herein.

Figure 6:
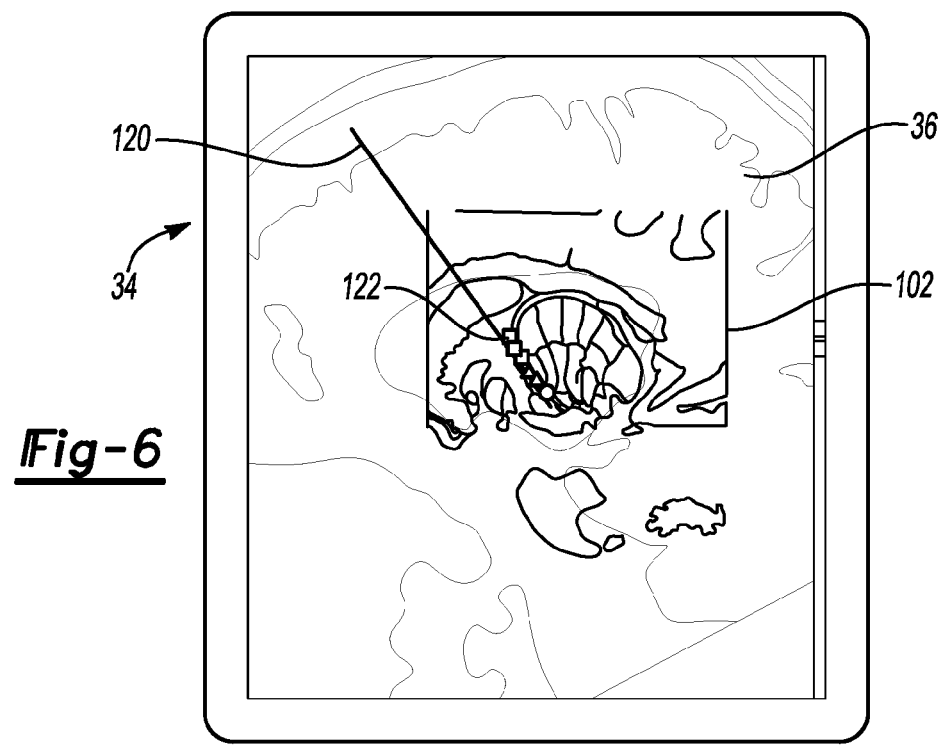
FIG. 6 is an illustration of various types of data including image data, physiological data, icon data, atlas data, according to various embodiments.

With reference to FIG. 6, various types of anatomical or physiological information can be collected using any appropriate system and can be provided as the data 2. For example, a micro-electrode recorder (MER) can be moved through the anatomy of the patient 14. The image data 36 can be displayed on the display 34 and a position of the MER, which can be the instrument 52, can be displayed as the MER icon 120. The MER icon 120 can be displayed or superimposed on the image data 36 and also on the atlas data 102. Although the atlas data 102 can assist in determining a position of a selected location in the image data 36, the MER can be used to assist in further refining a location within the anatomy of the patient 14. Additional icons, such as bread crumb icons 122 can be displayed superimposed on the image data 36, the atlas data 102, etc. to illustrate various changes or sensed anatomical locations based upon the information recorded by the MER. The bread crumbs 122 can assist in determining a selected region, such as a functional or anatomical region, within the image data 36. A generally known recording for a selected region of the anatomy can be recorded with the MER 120 to verify the identity of an anatomical or functional portion and a location of the MER 120 can be determined via the navigation system 10. The determined location of a selected region, such as the thalamus, can be detected with the MER and can be displayed on the display 34 with one of the bread crumbs 122. The atlas location from the atlas data 102 can then be refined when being superimposed on the image data 36 of the patient 14. Also, refinement of the atlas data 102 can also be used to refine the location of other atlas or mapped locations that are illustrated with the atlas data 102.

The data used to refine the atlas data 102 or the data 2 can also be used during an operative procedure. The anatomy and neurophysiology that is depicted by the atlas data 102 and the plan created may show the probe as navigated in one location, but the intra-operative functional data may confirm it to be in another location (due to clinical shifting, etc.). To determine the next steps, or help refine a trajectory, path, or treatment should be chosen for the therapy, the atlas data 102 can be manipulated to match the intra-operative functional and observed data It will be understood that any appropriate recording or sensing device can also be used in addition or alternatively to the MER. Other appropriate or selected sensing probes, such as an optical coherence sensor, or the like can be used to provide an appropriate anatomical or functional landmark or structure information. The atlas 102 can be enhanced or further augmented based upon the probe information to assist in determining an appropriate transformation or customization of the atlas relative to the image data 36. It will be further understood that the atlas data can be the 3D atlas data 100 or any other appropriate atlas data and need not necessarily be the 3D atlas data.

As discussed above, the atlas data, which can include the 3D data 100 or 2D data 102, can be provided. The 2D and 3D data can be displayed for viewing on the display device 34.

Further, the atlas data information can be registered with the patient image information. The registration can include custom patient alignment. For example, the anterior commissure and the posterior commissure can be determined with Talairach scaling. Also, basal ganglia and local non-linear alignment or global non-linear alignment can be determined. The data can be used for digital mapping of the selected portion of the anatomy, such as the brain. Further, automatic fit or cell types can be determined. That is, cell types in the image data can be determined and displayed on the display 34 for use by the user 67. In addition, the MER can be used for automated fitting, such as by determining or assisting the determination of different cell types or anatomical or functional regions and fitting the atlas 100, 102 to the image data 36. In addition, back projection of physiology or back projection of therapeutic contacts can be used in physical atlases.

The atlas data allows for the statistical or general mapping or indication of various portions of the anatomy, such as portions in the brain, portions in the spinal cord, various anatomical features, or the like. Atlas data can be based upon various procedures or studies, such as well understood and studied anatomical scans. For example, the Schaltenbrand-Wharen or Talairach atlases are generally accepted and well understood atlases of the human brain. Portions that are identified within the Schaltenbrand-Wharen or Talairach atlases can be the atlas data that is used, as discussed above, and herein.

The atlas data can be used at any appropriate time. For example, the atlas data can be superimposed or registered to the image data of the patient for planning a procedure. The atlas data can also be superimposed or registered to the image data for use during a procedure, such as to assist in navigation. The additional instruments, such as the MER, can be used to verify the locations of various portions of the anatomy based upon the atlas data. The MER can be introduced into the brain to record activity within the brain to confirm locations identified with the atlas data.

The feedback loop 6 in the optimization procedure 1 can be used to enhance the atlas data. The atlas data can be stored in the memory system, or any appropriate memory system, and can be augmented based upon information from the procedure or post procedure follow-up. The detected or confirmed location of an anatomical feature or target, can be used to augment or provide a statistical range of the atlas data for use in future procedures. It will be understood, the atlas data can represent any appropriate data 2.

The atlas data can also be used post operatively. For example the atlas data can be superimposed onto image data acquired post operatively of a patient. The atlas data can be used to confirm long time positioning of various implants or instruments, such as DBS leads. Therefore, the atlas data can be used at any appropriate time relative to a procedure time.

Figure 7:
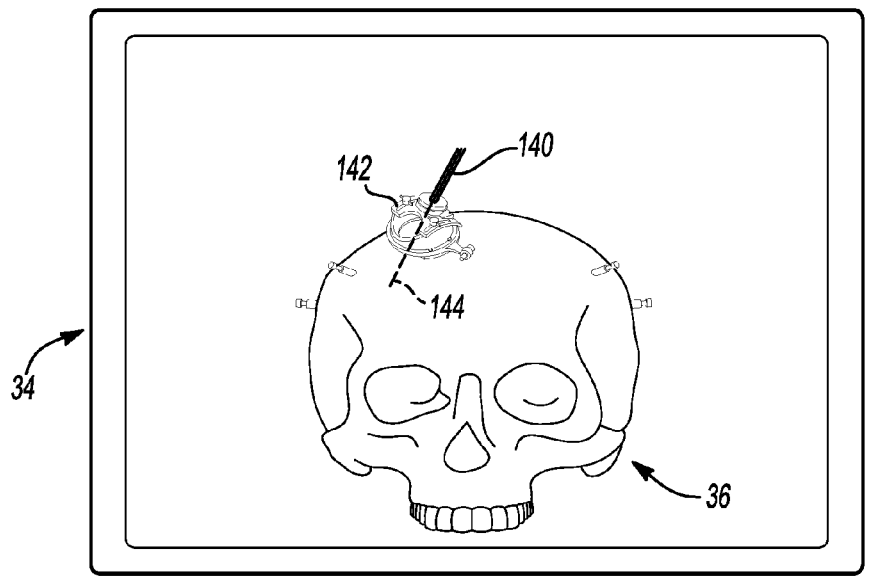
FIG. 7 is an illustration of tracking and positioning of a device relative to an anatomy.

With reference to FIG. 7, the image data 36 can be displayed on the display 34. The instrument 52 can include a deep brain stimulation probe 140. The DBS probe 140 can be the instrument 52 being tracked for determining its position in the brain. In addition, the stereotactic frame 80 can be provided according to various embodiments as an aiming device 142. According to various embodiments, including those discussed above, a tracking device can be positioned relative to the DBS probe. For example, a tracking device can include a small electromagnetic coil positioned at a tip 144 of the DBS probe 140. In addition, the stereotactic or aiming device 142 can be tracked by the tracking system 44 for navigation with the navigation system 10. Regardless, the location of the tip 144 of the DBS probe 140 can be displayed relative to the image data 36. For example, an icon can be displayed on or relative to the image data 36 for illustration of the position of the tip 144 of the DBS probe while performing the procedure in block 4.

The provision of the various atlas data 100, 102 and the image data 36 of the patient 14, including other information, such as the physiological data from block 2c, can assist in registration and determination of various targets and an appropriate aiming of the aiming device 142. In addition, the tip 144 of the DBS probe 140 can be substantially precisely tracked due to various elements, such as the positioning of the tracking device 58 at the tip 144, the aiming device 142, or other appropriate mechanisms. Regardless, the exact location of the tip 144 can be navigated relative to a selected portion of the patient 14, such as the target 104, 106 defined during the planning procedure. This can allow for determination or correct placement of a select instrument, such as a DBS probe. It will be understood that any appropriate instrument can be positioned relative to the patient 14 and the DBS probe is merely exemplary. However, the precise positioning, in addition to determination of the appropriate target based on the data provided as discussed above, can assist in performing the appropriate procedure.

Although the procedure can be navigated, as illustrated in FIG. 7, direct visualization can occur via the imaging system 12 or any appropriate imaging system. Returning reference to FIGS. 2, 2A and 2B, the navigation system 10' can include an alternative imaging device 12', such as an intraoperative MRI system 12' (FIG. 2A) or O-arm™ imaging system 12" (FIG. 2B). A work station 31' can be provided to control various portions, such as the alternative imaging device 12', and the optical localization system 44". Therefore, one skilled in the art will understand that the appropriate navigation system can be provided and the navigation systems 10, 10' are merely exemplary. Further, direct visualization can be used to assist in the performing of the selected procedure. Therefore, navigation, with or without images, is merely exemplary and can be used to assist the user 67 in performing a selected procedure.

As illustrated in FIG. 7, the instrument 52 can include a the DBS 140. When positioning the DBS probe 140, it can be navigated with an electromagnetic navigation system or electromagnetic tracking system, as discussed above. In addition, the DBS probe 140 or any appropriate instrument can be positioned with no line of sight navigation. This can include positioning or navigation of the instrument simply by navigating the instrument based upon the various visualization techniques, including the image data obtained of the patient and registered to various atlas information or other appropriate systems.

Further, the image data can be used for navigation by the user 67 with the navigation system 10, 10' in any appropriate manner. As discussed above, fiducials 60 can be provided for use to register patient space to image space. Alternatively, or in addition thereto, substantially fiducial less registration can be provided. Fiducialless registration can include providing an imaging system 12, 12', 12" integrated with the tracking system 44, 44', 44". The imaging system 12, 12', 12" can be integrated into the tracking system 44, 44', 44" so that the position of the imaging device 12, 12', 12" is known by the tracking system 44, 44', 44" so that the navigation system 10, 10' acts as one system. In this case, fiducials may not be required to register the image data with the patient space.

In addition, substantially automatic registration can include positioning the tracking device 54a substantially on the top or integrally with the fiducial 60 During the acquisition of the images, the fiducial 60 is present and the tracking device 54a can be interconnected with the fiducial 60 or at substantially the same location after imaging. Therefore, the tracking system 44 can determine the position of the tracking device 54a once the patient 14 is moved into the localization field and substantially automatic registration can occur if the fiducial points in the image data are determined.

With integration of the imaging system and the tracking system, the integrated navigation system can be provided for post-operative confirmation. That is the navigation system can be used to confirm the positioning of the instrument, such as the DBS probe 140, in the procedure. The post-operative confirmation can be substantially immediately post-operative or at a later time, but can be used to ensure the appropriate positioning of the probe 140. The position of the probe 140 can again be determined based upon the atlas information, which can be provided relative to post-operative image data or any other appropriate system.

As discussed above, any appropriate procedure can occur. For example, the positioning of a deep brain stimulation probe 140 can be performed. As is generally known in the art, the deep brain stimulation probe is then programmed or can be programmed post-operatively to apply a selected therapy, such as a voltage to the area of the anatomy relative to positioning of the probe. It will be understood, however, that any other appropriate therapy can be provided, such as a pharmaceutical delivery, a gene or cell therapy, a radiation therapy, or the like. The exemplary discussion of a deep brain stimulation programming is provided for illustration. Further, as discussed above, the appropriate positioning of the deep brain stimulation probe can be provided based upon atlas data, physiological, or patient specific data (e.g., image data of the patient, physiological data of the patient, MER data of the patient, optical coherence tomography data of the patient).

Figure 8:
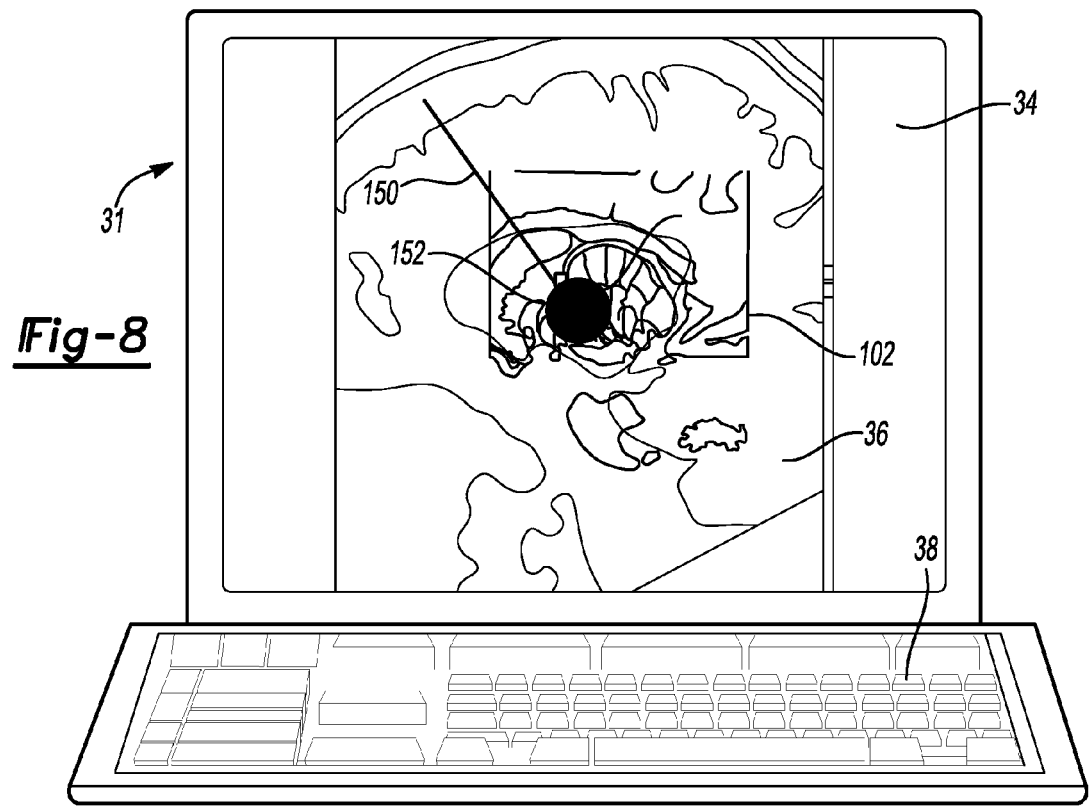
FIG. 8 is a perspective view of a work station including a display displaying various types of data according to various types of embodiments.

With reference to FIG. 8, the various physiological data can be provided with any appropriate system, such as the MER, optical coherence tomography, or the like. Further, these various instruments can be tracked with the tracking system 44, 44', 44'' as discussed above. Therefore, the exact position of various portions of the anatomy, such as portions of the brain, can be determined and sensed with the various sensing probes or recorders. This can allow the image data to be substantially real time mapped for use in the procedure in block 4. For example, the atlas data 102, 104 can be substantially real time updated, morphed or translated for use during the procedure with sensing probes, such as the MER. This can assist in determining an exact location of various anatomical structures or functional structures for assisting in determining a selected position to implant the DBS probe 140, or any appropriate system or implant. The determination of physiological data can assist during a procedure to ensure an appropriate identification of a selected anatomical or functional structure and can assist in updating, in substantially real time, a selected physical or functional map of the anatomy. Tracking the instrument while determining the physiological feature assists in its appropriate determination and location.

The placement and appropriate therapy can be determined using the various data, such as the patient specific data, including physiological image data, and atlas data. For example, the work station 31, illustrated according to various embodiments in FIG. 8, can include the display 34 that displays the image data 36 and the atlas data 102. Further, displayed relative to the image data 36 and the atlas data 102 can be an icon 150 illustrating a position of the DBS probe 140 in the anatomy. The illustration of the probe as the icon 150 can also be provided for substantially post-operative programming of the implant.

It will be understood that the position of the probe in the anatomy can be determined in any appropriate manner, such as based upon the navigation during the procedure, based on post-operative imaging of the patient, based on post-operative tracking of the tracking sensor, or any appropriate manner. Nevertheless, the determination of the position of the probe and its illustration as the icon 150 relative to the image data 136 can be used to assist in programming the DBS probe or lead in an appropriate manner. Further, the various data collected during the procedure can also be illustrated relative to the image data 36 and the atlas data 102, such as the neurophysiological data that can be collected with the various instruments, such as the MER or optical coherence tomography. This information, including the physiological data, functional data, and location data, can also be used for later programming and operation of the DBS lead. For example, the location of the lead relative to a functionally identified region of the anatomy can be used to assist in programming the amount of therapy to be delivered from the lead.

With continuing reference to FIG. 8, the workstation 31 can be used to program an implant, such as the DBS probe or lead. It will be understood that the workstation 31 can be the workstation 31 used during the navigation or can be any appropriate workstation. The workstation 31 can allow programming of the DBS probe in a generally known manner. Information from the procedure during which the implantation of the instrument occurred can be used. Further, the data from block 2 of the optimization procedure can be used to assist in the programming of the implants. Programming the implants can include determining a voltage level, determining a pulse width, frequency, power level, frequency, or other features. The information from the procedure, such as the exact location within the brain, the determined anatomical or functional structures near the position of the implant, or the like can be used in programming the implants. Therefore, the information obtained during a procedure can be used both in a general statistical sense, for use with other patients, and for use in post-operative work on a specific patient.

Figure 9A:
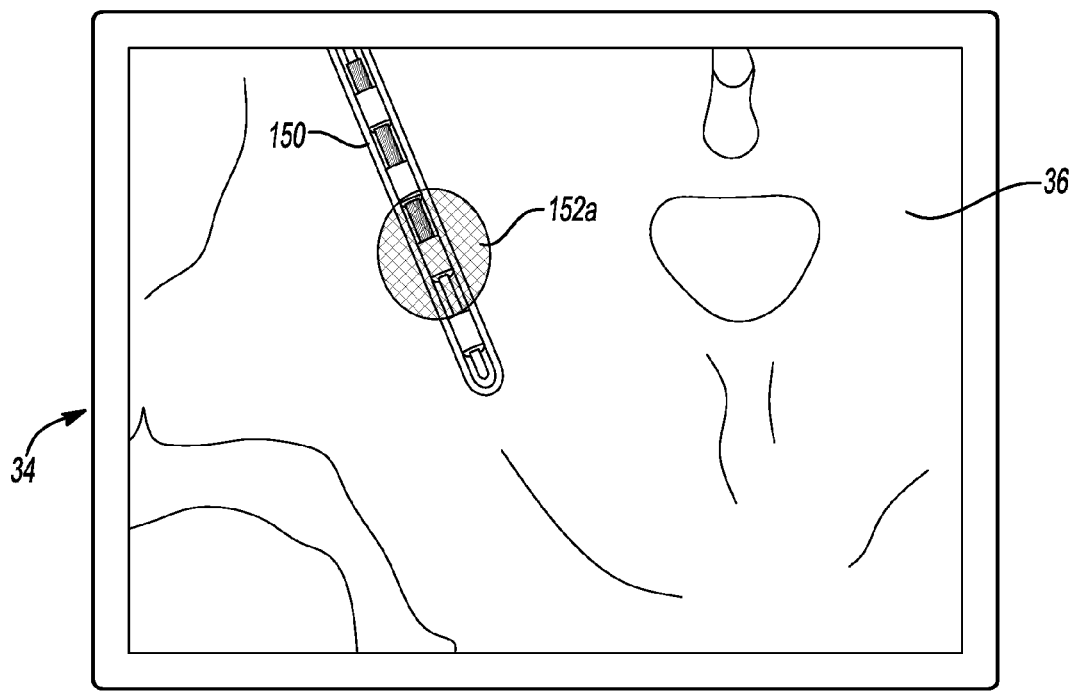
FIG. 9A is an illustration of an affect of a therapy according to various embodiments.
Figure 9B:
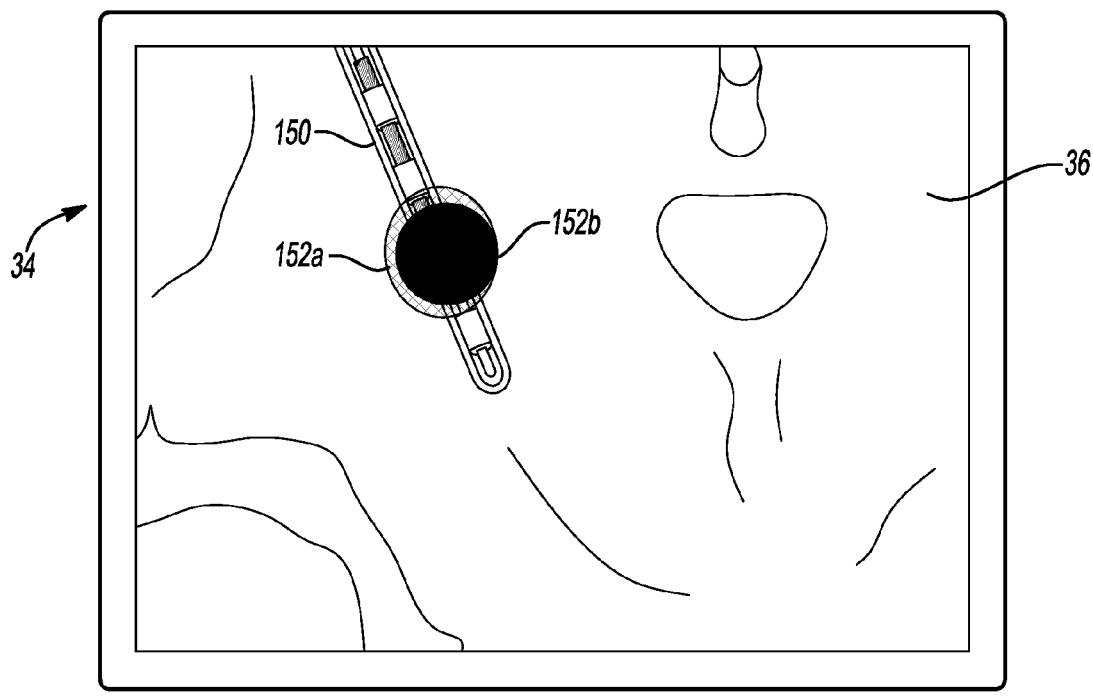
FIG. 9B is a display of image data including an icon representing an affected area according to a selected therapy according to various embodiments.

With reference to FIGS. 9A and 9B, the display of the image data 36 including the icon 150 of the DBS probe can be illustrated relative to a first therapy icon 152a. It will be understood that the representation of the atlas 102 can also be included if selected, and its absence from FIGS. 9A and 9B is merely for clarity of the illustration. Nevertheless, when the probe is being programmed, which can occur substantially intraoperatively or post-operatively, a selection of a voltage, a pulse width, or other appropriate programmable features, including a selection of appropriate leads can be used.

The therapy icon 152a can illustrate an assumed or predicted treatment affected area. The therapy icon 152a can illustrate a size, density amount, etc. of the therapy. The therapy icons, according to various embodiments, generally illustrate a localized affect on the anatomy. The localized affect or treatment area can be based upon the data 2. Generalized affects on the patient can be determined after the therapy is applied, such as reduction of Parkinson's disease symptoms.

The first or initial therapy icon 152a can illustrate an affected area based upon a selected or programmed therapy for viewing by a user, which can include the surgeon 67. It will be understood that the initial therapy icon 152a can illustrate a size, a geometry, a density, and the like of the therapy that is selected or programmed. It will be understood that the initial icon 152a can merely be a virtual representation of the predicted effect of a selected therapy. In addition, it will be understood that the image data 36 and the various icons can be two-dimensional, three-dimensional, four-dimensional or the like. Therefore, the representation of the two-dimensional image data 36 and the two-dimensional initial therapy icon 152a is merely exemplary. Nevertheless, the initial therapy icon 152a can illustrate the possible or selected affect area of a selected therapy on the anatomy.

Turning to FIG. 9B, the image data 36 can be illustrated with the probe icon 150 and a secondary therapy icon 152b. The secondary therapy icon 152b can illustrate a predicted affect of a second selected therapy, such as a higher pulse width. The higher pulse width may affect a higher density or higher number of cells within a selected geometrical region. Therefore, the second therapy icon 152b can illustrate or graphically illustrate the higher density of the cells being affected. Therefore, the initial therapy icon 152a can be substantially transparent while the second therapy icon 152b may be substantially opaque.

The icons 152a, 152b can illustrate representation of a possible or selected therapy on the patient prior to instigating a therapy on the patient. This can allow for substantially a graphical programming of the implant to make the programming of the implant more efficient and require fewer attempts to obtain an optimal therapy. The predicted affect using the therapy icons 152a, 152b can also be used during the procedure to ensure that an instrument is positioned in an appropriate location for the selected or predicted therapy.

The therapy icons 152a, 152b, according to various embodiments, can be used to predict an area that will be affected by therapy, ensure that an instrument is implanted in the appropriate location for providing a therapy, or a procedure to position an instrument to provide a therapy. Therefore, it will be understood, that the therapy icons are not only provided for a single part of the procedure, but can be provided for multiple parts of the procedure. The therapy icons can be used to plan a procedure, perform a procedure, and post operatively to provide a treatment to the patient. In any of these situations, the icons can be displayed on the display device for use by the user 67 to optimize the therapy for the patient 14.

Figure 10A:
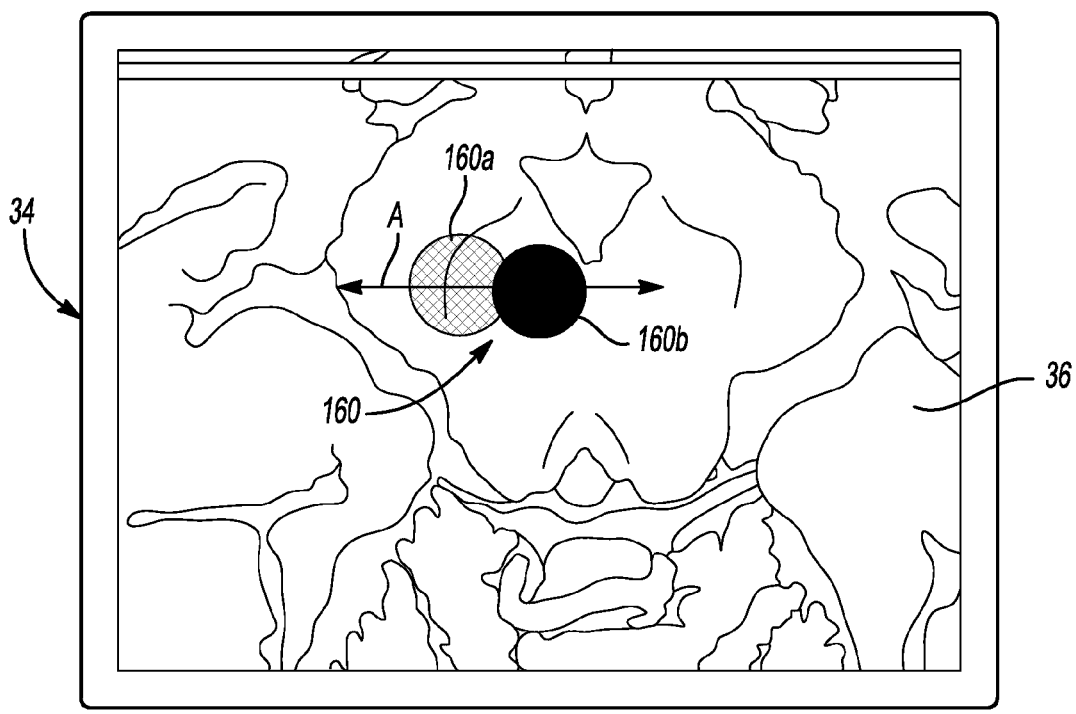
FIG. 10A is image data including an icon representing a selected therapy's affect on the anatomy.
Figure 10B:
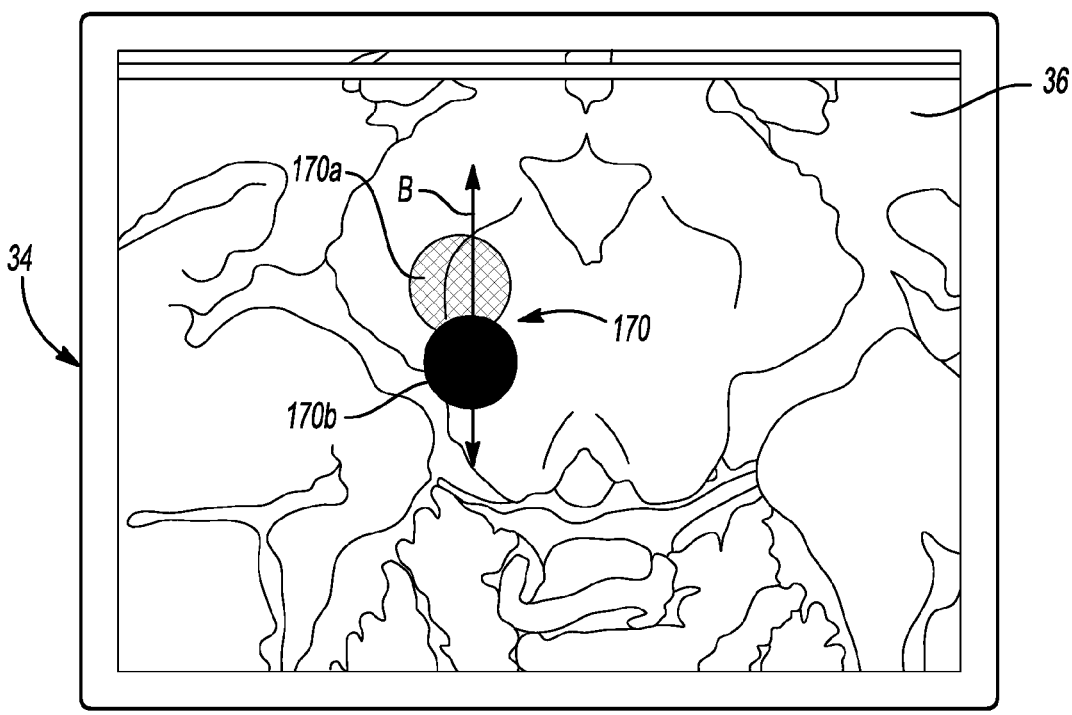
FIG. 10B is an illustration of image data with an icon representing an area of the anatomy affected by a selected therapy.

In addition to a therapy density, a therapy field of shape, depth, or other geometry can also be selected and visualized. With reference to FIGS. 10A and 10B, and initially to 10A, the image data 36 can be illustrated relative to a second initial therapy icon 160. The second initial therapy icon can include two lobes or portions 160a and 160b. The two portions 160a, 160b of the second initial therapy icon 160 are merely exemplary of any appropriate or possible geometrical shape. Nevertheless, the second initial therapy icon 160 can illustrate that a proposed or selected therapy will affect a region generally having a longitudinal axis A. The longitudinal axis A may be provided relative to the image data 36 for viewing by the user 67. The longitudinal axis A and the icon portions 160a, 160b can be used by the user to determine whether a selected geometrical area is appropriate for the provided therapy. Further, the icon portions 160a, 160b can also include differing opacities to represent different densities of the therapy.

With reference to FIG. 10B, a secondary therapy icon 170 is illustrated. The second secondary therapy icon 170 can include a first portion 170a and a second portion 170b. The two portions 170a and 170b can define a longitudinal axis B relative to the image data 36. The longitudinal axis B can be different than the longitudinal axis A, such as including a different angle relative to the image data 36. Although the icon portions 170a, 170b can include different opacities or similar opacities, the icons can represent a different geometrical shape relative to the image data 36 of the patient 14. The different geometrical shapes can illustrate a different geometrical application of the therapy relative to the patient, illustrated in the image data 36.

The therapy icons can be illustrated in any appropriate orientation relative to the image data or atlas data. The illustration of the therapy icons, whether to illustrate a different size, different therapy type, different therapy amounts, or the like can be illustrated for procedure planning, procedure performance, or post operative treatment provisions. Moreover, the therapy icons can be illustrated to assist a user in determining an appropriate or optimal therapy provision. For example, the user can view on the display device the predicted therapy and determine the effect of the treatment on the patient. Therefore, the therapy icons can be used to determine whether a predicted therapy is having a predicted affect on the patient 14.

It will be understood that the various icons 152, 160 and 170 can represent two-dimensional, three-dimensional, four-dimensional, or any appropriate geometrical shapes. The icons provide a graphical representation of a proposed or selected therapy on the image data 36 of the patient 14. The icons 152, 160, 170 can illustrate a depth, geometry, affected area, amount of affected cells, charge over time, etc. of the selected therapy. The graphical representation can be used by the user 67 to assist in determining the appropriateness of the selected therapy. In addition, the graphical representation can be used to ensure that the therapy is being provided to an appropriate location within the anatomy. Again, the provision of the atlases 102, 104 can assist in this. Also, the various data that is determined intraoperatively or post-operatively, such as the physiological data, can be used to ensure or augment or customize the atlases relative to the particular patient 14. Therefore, the image data 36 during the programming phase in block 5 can also be illustrated or displayed relative to the atlas data to assist in determining whether the therapy is being applied to a selected or appropriate location.

Thus, one skilled in the art will understand that the optimization system 1 can be used to assist in all of a preoperative planning, an intraoperative procedure, and a post-operative follow up or programming. The programming can be of any appropriate system, such as the deep brain stimulator, a therapy application, a pacer, or any appropriate implant system. In addition, the optimization system 1 can include any appropriate or be used with any appropriate navigational or imaging system to assist in obtaining the appropriate image data. Also the various probes or sensors, such as the MER, can be used to assist in customizing an atlas relative to the particular patient to assist in locating or determining appropriate anatomical or functional regions.

The optimization system 1, diagrammatically illustrated in FIG. 1, and taught and described above, can be provided with a substantially graphical user interface (GUI) to assist in performing a procedure. As illustrated in FIG. 11, a system with a selected GUI can be provided for use with the system 1. The various illustrations include exemplary screen shots from the work station 31. The image data 36 can be provided on the display 34 for manipulation by a user employing the user input 38. As illustrated above, various types of data can be provided that include those graphically illustrated in block 202 in FIG. 11. It will be understood that additional information can also be provided, including an optical coherence data, illustrated in FIG. 12 below. The optical coherence data 220 can be displayed relative to a graphical or diagrammatic representation of the brain 221 and an instrument obtaining the optical coherence data.

The data, with reference to FIGS. 11 and 12, can include image data 36 and an initial atlas fitting, such as the two-dimensional atlas 102. In addition, various types of physiological data can be provided, such as with an MER that can create or report an electrical signal 204. The electrical signal 204 can be illustrated on the display 34 and can also be illustrated relative to a diagram or position of the MER, in the anatomy of the patient 14 relative to the image data 36. A substantially pre-registered or custom display of the atlas data can be provided or illustrated at block 206. The various data, such as data recorded by the MER can be illustrated as various icons 208. The various icons 208 or the data recorded by the MER can be used to create a substantially custom or real time registration or morph of the atlas data 102 to the image data 36 of the patient. This can allow substantially real-time registration of the atlas 102 to the patient data 36. This can also allow for a substantially precise locating or positioning of various portions, such as a deep brain stimulation probe relative to the patient using the image data 36.

A graphical planning can be provided based upon the various data collected either intraoperatively or preoperatively. The planning, graphically illustrated at 210, can occur at any appropriate time, as discussed above. Further, the planning or planned procedure can be changed substantially intraoperatively based upon obtained information, including the substantially real time registration or morphing of the atlas data 102 to the patient data or image data 36.

The various types of data can then be used to assist in programming or selecting a particular therapy. The optimization programming of block 5 is graphically illustrated in block 212. As discussed above, the various graphical displays can illustrate icons that illustrate how a therapy is predicted to affect various portions of the anatomy and can be used to substantially, precisely and efficiently program a particular therapy, such as a deep brain stimulation, cell therapy, gene therapy, or the like. Nevertheless, the icons can assist in determining or illustrating how a therapy will likely affect various portions of the anatomy and can be used to assist in more precisely or efficiently programming the system. Also as discussed above, the illustration of how a therapy might affect the anatomy can be used in planning the procedure, such as selecting an appropriate target, trajectory, or the like.

Moreover, the target can be reached based upon a linear or non-linear path. Optimization of a therapy can include determining the appropriate path and trajectory to reach a selected location in the anatomy. Again, the data 2 can assist in identifying regions of the anatomy to provide a treatment to and assist in identifying the trajectory or path to reach the target for therapy.

One skilled in the art will understand that the predicted affected or therapy icons illustrated an empirical physiological effect. The actual effect on the patient's symptoms can differ from patient to patient. Therefore, the icons can be used in future models and also to determine an amount or location of treatment provided to a selected patient. As the therapy for the selected patient is refined, reference can be made to the previous therapy areas or type illustrated with the icons.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A method of performing a procedure on an anatomy of a patient, comprising:
    selecting a position for the procedure within the anatomy;
    proposing a first therapy;
    obtaining a first data set including image data and functional data regarding the anatomy and registering the obtained image data to the anatomy at least by:
        identifying a specific functional feature of selected anatomical portions within the anatomy, and
        determining a location of the specific functional feature in the obtained image data at least by determining a position of a navigated functional sensing device, which is configured to sense the functional data regarding the specific functional feature within the anatomy and is associated with a tracking system including a localizer and a tracking device, based upon a tracked location of the tracking device;
    planning the procedure at least in part with the obtained first data set regarding the anatomy;
    navigating an instrument that is a deep brain stimulation lead to the selected position;
    superimposing a first predicted physiological affect icon on an image of the anatomy based on the obtained image data to illustrate a graphical representation of a predicted first localized affect on the anatomy of the patient of the first therapy as the first therapy is performed; and
    performing the first therapy on the anatomy at the selected position with the navigated instrument wherein the first therapy includes effecting the physiology of the anatomy.

2. The method of claim 1, further comprising:
    obtaining a second set of data regarding the anatomy after performing the first therapy;
    proposing a second therapy operable to effect a physiology of the anatomy;
    illustrating a predicted second localized physiological affect of the proposed second therapy on the anatomy which is a graphical representation of a predicted second localized physiological affect of the proposed second therapy; and
    performing the second therapy on the anatomy.

3. The method of 2, further comprising:
    determining a first general effect of the first therapy on the anatomy;
    wherein the second therapy is at least one of identical to the first therapy, different than the first therapy, or combinations thereof.

4. The method of claim 3, further comprising:
    augmenting the second therapy compared to the first therapy so that the second therapy is different from the first therapy;
    wherein the different second therapy includes a different electrical voltage, a different electrical pulse width, a different chemical delivered, a different dosage delivered, a different electrical lead activated, or combinations thereof.

5. The method of claim 3, further comprising:
    determining a second general effect of the second therapy on the anatomy;
    comparing the determined first general effect and the determined second general effect; and
    determining an optimized therapy on the anatomy.

6. The method of claim 5, wherein the optimized therapy can be the same as the first therapy, the same as the second therapy, different from either of the first therapy or the second therapy, or combinations thereof.

7. The method of claim 1, further comprising:
    performing a second therapy on the anatomy;
    wherein the instrument includes a plurality of instruments;
    wherein performing the first therapy includes performing the first therapy via a first sub-plurality of the plurality of the instruments and performing the second therapy includes performing the second therapy via a second sub-plurality of the plurality of the instruments.

8. The method of claim 1, further comprising:
obtaining database data;
wherein illustrating a first localized physiological affect of a first therapy includes predicting a localized physiological affect based on the database data and at least one of optical coherence tomography data, temperature data, hydraulic data, or electrical data.

9. The method of claim 8, further comprising:
determining a specific current localized physiological effect on the anatomy due to the first therapy and after performing the first therapy on the anatomy; and
augmenting the database data to form an augmented database data including the determined specific current localized physiological effect on the anatomy due to the first therapy;
wherein the specific current localized physiological effect on the anatomy is based on a physical measurement of the anatomy at the selected position of the procedure within the anatomy where the first therapy is performed.

10. A method of performing a procedure on an anatomy of a patient, comprising:
providing image data of a specific patient;
providing a first database data including statistical information regarding an anatomy similar to the specific patient;
performing an initial registration of the provided image data of the specific patient and the first database data;
obtaining functional physiological data of the specific patient;
refining the initial registration, at least by increasing an accuracy of the initial registration, of the provided image data of the specific patient and the first database data based at least in part on the obtained functional physiological data of the specific patient, wherein the provided first database data includes statistical functional physiological data regarding specific areas of the anatomy;
performing a procedure on the specific patient, including:
navigating an instrument that is a deep brain stimulation lead relative to the specific patient;
displaying a representation of the navigated instrument relative to the provided image data of the specific patient; and
forming a second database data for performing the procedure on the specific patient or a different patient other than the specific patient at least by augmenting the provided first database data with at least one of the obtained functional physiological data of the specific patient or the provided image data of a specific patient at least by altering a statistical functional data point from the provided first database data, wherein the statistical functional data point is used to assist in identifying a region in the provided image data of a specific patient.

11. The method of claim 10, further comprising:
implanting the deep brain stimulation lead in the specific patient; and
programming the deep brain stimulation lead based upon the formed second database data to provide a therapy to the specific patient after implantation of the device.

12. The method of claim 11, wherein programming the deep brain stimulation lead includes at least one of selecting a dosage voltage, selecting a pulse width, selecting a material to be delivered, or selecting a volume of a material to be delivered.

13. The method of claim 11, wherein implanting the deep brain stimulation lead includes implanting the deep brain stimulation lead into a brain of the specific patient, wherein the deep brain stimulation lead is operable to deliver an electrical potential to the brain;
wherein programming the device includes at least one of selecting a dosage voltage, selecting a pulse width, or combinations thereof.

14. The method of claim 13, wherein the statistical functional data point includes functional data used to assist in identifying a region in the provided image data of a specific patient, wherein the functional data includes at least one of microelectrode recording data, pressure data, or gating data.

15. The method of claim 14, further comprising:
executing instructions with a processor to perform a registration of the provided image data of a specific patient and the formed second database data; and
identifying a target in the anatomy of the patient in the registered image data of a specific patient and the formed second database data.

16. The method of claim 15, wherein forming a second database data includes determining an average location of an anatomical feature based upon information from a plurality of patients.

17. The method of claim 10, wherein providing the initial registration of the provided image data of the specific patient and the first database data includes morphing the provided image data of the specific patient to fit the first database data;
wherein refining the initial registration includes:
identifying specific functional features of selected anatomical portions of the specific patient; and
determining a location of the specific functional features in the provided image data of a specific patient.

18. The method of claim 17, further comprising:
providing a tracking system including a localizer and a tracking device associated with the navigated instrument;
wherein navigating the instrument includes determining a position of the instrument based upon a tracked location of the tracking device.

19. The method of claim 18, wherein the tracking device includes at least one of an optical tracking device, an electromagnetic tracking device, an acoustic tracking device, an accelerometer tracking device, a radiation tracking device, or combinations thereof.

20. The method of claim 18, further comprising:
displaying the refined registration of the provided image data of a specific patient and the first database data;
wherein displaying a representation of the navigated instrument includes displaying an icon representing the location of the navigatged instrument relative to the anatomy of the specific patient on a display device.

21. The method of claim 10, further comprising:
identifying a target based upon the refined initial registration of the provided image data of a specific patient and the provided first database data; and
providing a therapy to the target with the instrument.

22. A method of performing a procedure on an anatomy of a patient, comprising:
selecting a position for the procedure within the anatomy;
obtaining a first data set regarding the anatomy;
planning the procedure at least in part with the obtained first data set regarding the anatomy including:
selecting a first therapy type to be applied at the selected position in the anatomy;
predicting a first affect at the selected position in the anatomy of the first selected therapy type prior to performing the selected first therapy type;

illustrating a first localized graphical representation of the predicted first affect, wherein the first localized graphical representation is a first physiological affect icon superimposed on an image of the anatomy, wherein the first physiological affect icon illustrates an area of the anatomy predicted to be affected by the selected first therapy type, wherein illustrating the first localized graphical representation includes displaying the first physiological affect icon superimposed on the image data of a portion of a brain of the patient;

displaying an instrument icon representing a deep brain stimulation probe location based on a navigation of the deep brain stimulation probe into the brain of the anatomy of the patient; and augmenting the first data set with feedback based upon an observed result of performing the selected first therapy type on the brain at the selected position.

23. The method of claim 22, wherein the physiological affect icon includes a viewable feature that changes based upon the first therapy and the physiological affect icon is illustrated near the instrument icon.

24. The method of claim 23, wherein the physiological affect icon illustrates a predicted geometrical shape that the first therapy will affect accounting for at least one of voltage or pulse width.

25. The method of claim 24, wherein the physiological affect icon illustrates a predicted time lapse area of effect of the first therapy.

26. The method of claim 25, further comprising:
selecting a second therapy type;
predicting a second affect that is a region of the brain that the selected second therapy type will affect;
illustrating a second localized graphical representation of the predicted second affect, wherein the second localized graphical representation is a second physiological affect icon superimposed on an image of the anatomy, wherein the second physiological affect icon illustrates the region in the brain predicted to be affected by the selected second therapy type;
wherein the first physiological affect icon and the second physiological affect icon illustrate a predicted region that is to be affected by the selected respective first therapy type and the second therapy type, where the region predicted to be affected may represent a region affected by the respective selected first therapy type and the selected second therapy type.

27. The method of claim 26, wherein the selected first therapy is a first brain stimulation therapy and the selected second therapy type is a second brain stimulation therapy different from the first brain stimulation therapy;
wherein the first physiological affect icon has a first size, shape and density and the second physiological affect icon has a second size, shape, and density to illustrate the predicted difference of affected region of the brain between the first selected therapy type and the selected second therapy type.

28. The method of claim 27, further comprising:
selecting for patient treatment at least one of the selected first therapy type or the selected second therapy type based at least on the first physiological affect icon and the second physiological affect icon; and
programming a device to provide the selected patient treatment through the deep brain stimulation probe.

29. The method of claim 28, wherein selecting for patient treatment includes determining an optimal treatment for the patient from between the selected first therapy type and the selected second therapy type based on the first physiological affect icon and the second physiological affect icon.

30. A method for performing a procedure on an anatomy of a patient, comprising:
accessing a first memory system having a stored data including statistical information regarding the anatomy;
performing, by executing instructions with a processor system, a first registration of the patient to the stored data;
obtaining current functional patient specific data during the procedure at a determined location in the anatomy of the patient to determine a location of a selected region in the anatomy of the patient;
performing, by executing instructions with the processor system, a second registration of the patient to the stored data that refines the first registration of the patient to the stored data, wherein the second registration is based at least in part on the obtained current functional patient specific data including registering the selected region from the stored data to the patient based on the obtained current functional patient specific data;
displaying a view of at least one of an image of the patient or the stored data based on the second registration; and
tracking a deep brain stimulation lead into a brain of the patient to determine a location of the deep brain stimulation lead relative to the patient.

31. The method of claim 30, further comprising:
acquiring the image of the patient as a procedure image data of the patient during the procedure;
wherein performing both the first registration and performing the second registration includes registering the stored data to the acquired procedure image data of the patient acquired during the procedure;
wherein the stored data is acquired prior to the procedure and includes an atlas data, an average functional data, a patient specific functional data acquired prior to the procedure, or combinations thereof.

32. The method of claim 31, further comprising:
displaying the obtained current functional patient specific data after performing the second registration, wherein the current functional patient specific data includes functional data collected with a navigated measuring instrument;
determining a data target in the stored data and then determining a patient target in the anatomy of the patient based on the performed second registration; and
displaying an icon superimposed on the displayed obtained current functional patient specific data representing the determined target in the displayed obtained current functional patient specific data.

33. The method of claim 32, further comprising:
refining a location of an atlas location of the selected region in the brain of the patient based at least on the second registration that was previously identified in the atlas data and operable to be illustrated with the atlas data;
predicting a localized physiological affect of a proposed therapy in the patient based upon the stored data; and
displaying an affect icon superimposed on the image of the patient to represent the predicted localized physiological affect.

34. The method of claim 33, wherein the affect icon displays a localized physiological affect of the therapy selected from a group consisting of a voltage, a pulse width, a chemical volume delivered, a biological treatment delivered, a radiation treatment delivered, a therapy delivered over time, or combinations thereof.

35. The method of claim 34, further comprising:
wherein tracking the deep brain stimulation lead into the anatomy of the patient assists in the predicting of the localized physiological affect.

36. The method of claim 35, further comprising:
moving the deep brain stimulation lead into the brain of the anatomy of the patient, after obtaining the current functional patient specific data;
wherein predicting the localized physiological affect of the proposed therapy in the patient based upon the stored data includes predicting at least a first physiological affect of a first proposed therapy and a second physiological affect of a second proposed therapy; and
wherein displaying an affect icon superimposed on the image of the patient to represent the predicted localized physiological affect includes superimposing on the image of the patient a first affect icon based on the predicted first physiological affect of the first proposed therapy and superimposing on the image of the patient a second affect icon based on the predicted second physiological affect of the second proposed therapy;
selecting a present therapy as at least one of the first proposed therapy or the second proposed therapy based on the predicted affect of the respective first proposed therapy or the second proposed therapy;
applying the present therapy to the patient with the deep brain stimulation lead operable to be moved into the anatomy of the patient;
programming a treatment device to provide the present therapy through the deep brain stimulation lead, when implanted in the anatomy based, at least in part on the predicted localized physiological affect; and
displaying a treatment functional patient specific data icon illustrating an actual current effect of the applied present therapy.

37. The method of claim 32, further comprising:
illustrating bread crumb icons superimposed on image data to refine a location within the anatomy of the patient;
wherein the bread crumb icons illustrate changes based upon an information recorded by the navigated measuring instrument.

38. The method of claim 1, further comprising:
executing instructions with a processor to perform the registering of the obtained image data set with the anatomy; and
wherein selecting the position for the procedure within the anatomy includes identifying a target based upon the registering of the obtained image data of a specific patient and the provided first database data.

39. The method of claim 38, further comprising:
displaying the superimposed first predicted physiological affect icon on the image.

40. A method for performing a procedure on an anatomy of a patient, comprising:
determining the procedure;
obtaining a first patient specific data of a first patient regarding the determined procedure;
accessing a database data regarding the determined procedure by executing instructions with a processor;
determining a first plan for performing the determined procedure based upon the obtained first patient specific data of the first patient and the accessed database data;
performing the procedure on the anatomy of the first patient with an instrument that includes a deep brain stimulation lead;
obtaining a second patient specific data of the first patient while performing the procedure on the anatomy of the first patient; and
augmenting the database data based upon the obtained second patient specific data of the first patient obtained while performing the procedure on the first patient.

41. The method of claim 40, further comprising:
saving the augmented database data;
determining a second procedure; and
determining a second plan for the determined second procedure based at least upon the augmented database data.

42. The method of claim 40, wherein the determined second procedure and the determined second plan are regarding an anatomy of a second patient different from the first patient.

43. The method of claim 40, further comprising:
displaying the obtained first patient specific data including image data of a brain in the anatomy of the first patient;
selecting a therapy to apply to the brain in the anatomy of the first patient;
predicting a localized physiological affect of the therapy in the brain in the anatomy of the patient based at least in part on the accessed database data including atlas data having statistical information regarding regions of the atlas data relating to the determined first plan; and
executing instructions to illustrate the predicted localized physiological affect of the therapy on the brain, based at least on the accessed database data, as an icon superimposed on the displayed image data of the anatomy of the first patient.

44. The method of claim 43, wherein determining the first plan for the determined procedure, includes:
selecting a target in the brain in the anatomy of the first patient;
determining a trajectory of the instrument to reach the selected target; and
determining a therapy to be applied to the brain in the anatomy of the first patient via the instrument.

45. The method of claim 44, wherein determining the trajectory includes automatically determining at least a path for the instrument to take to reach a selected region of the anatomy of the first patient from an entry point into the anatomy of the first patient.

46. The method of claim 45, further comprising:
navigating the instrument to achieve the determined first plan;
tracking a tracking device associated with the instrument with a tracking system having a localizer;
determining the location of at least a portion of the instrument relative to the brain in the anatomy of the first patient;
illustrating a physiological affect icon relative to an instrument icon to illustrate at least one optical coherence tomography data, temperature data, hydraulic data, electrical data, or gating data based on the determined therapy to be applied to the brain.

47. The method of claim 45, wherein the obtained first patient specific data includes obtaining first patient specific image data;
wherein determining an entry point includes determining an entry point with the obtained first patient specific image data and wherein determining a path includes determining a path with the obtained first patient specific image data.

48. The method of claim 47, further comprising:
navigating the instrument relative to the anatomy of the first patient;

superimposing an instrument icon on the obtained first patient specific image data representing the position of the instrument relative to the anatomy of the first patient; and illustrating a physiological affect icon relative to the instrument icon to illustrate a physiological affect in the brain of the determined therapy to be applied to the brain;

wherein the physiological affect icon is operable to change based upon the determined therapy applied with the instrument.

49. The method of claim 48, further comprising:

providing a display device operable to display the obtained first patient specific image data and the physiological affect icon;

imaging the first patient with an imaging system to obtain the obtained first patient specific image data;

providing a tracking system including a localizer and a tracking device; and tracking a position of the instrument with the tracking system.

50. The method of claim 40, further comprising:

performing the determined procedure based on the determined first plan for the determined procedure, including navigating an instrument to a planned position within a brain of the first patient as a part of the determined first plan and implanting the instrument into the brain of the first patient;

illustrating a plurality of predicted therapy icons on a display as icons superimposed on a first patient specific image data of the first patient based on the accessed database data including atlas brain data including information regarding a physiology of the atlas brain, wherein the predicted therapy icons illustrate predicted affects of various specific programming parameters of the instrument in the brain;

programming the instrument to provide a therapy based at least in part on the illustrated plurality of predicted therapy icons; and performing the programmed therapy on the anatomy, including at least one of electrically stimulating the anatomy, providing a chemical therapy to the anatomy, providing a biological therapy to the anatomy, providing a radiation based therapy to the anatomy, or combinations thereof.

51. The method of claim 50, wherein illustrating a plurality of predicted therapy icons on a display as icons superimposed on patient specific image data of the first patient includes illustrating icons superimposed on patient specific image data of the brain of the first patient.

52. The method of claim 51, wherein obtaining first patient specific data includes at least one of obtaining image data, obtaining functional data, obtaining gating data, obtaining patient history data, or combinations thereof.

* * * * *

UNITED STATES PATENT AND TRADEMARK OFFICE
CERTIFICATE OF CORRECTION

| | |
|---|---|
| PATENT NO. | : 8,660,635 B2 |
| APPLICATION NO. | : 11/683796 |
| DATED | : February 25, 2014 |
| INVENTOR(S) | : David Simon et al. |

It is certified that error appears in the above-identified patent and that said Letters Patent is hereby corrected as shown below:

In the Claims

Column 24, line 35, Claim 3, "The method of 2, further comprising" should read -- The method of claim 2, further comprising --

Signed and Sealed this
Seventeenth Day of February, 2015

Michelle K. Lee
*Deputy Director of the United States Patent and Trademark Office*